(12) United States Patent
Olin et al.

(10) Patent No.: US 9,364,505 B2
(45) Date of Patent: Jun. 14, 2016

(54) THERAPEUTIC COMPOSITION FOR TREATMENT OF GLIOBLASTOMA

(75) Inventors: Michael Raymond Olin, Saint Paul, MN (US); Walter Low, Saint Paul, MN (US); John R. Ohlfest, Saint Paul, MN (US); Karen H. Ohlfest, legal representative, Roseville, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 314 days.

(21) Appl. No.: 13/881,712

(22) PCT Filed: Oct. 25, 2011

(86) PCT No.: PCT/US2011/057654
§ 371 (c)(1),
(2), (4) Date: Aug. 12, 2013

(87) PCT Pub. No.: WO2012/061120
PCT Pub. Date: May 10, 2012

(65) Prior Publication Data
US 2013/0323300 A1 Dec. 5, 2013

Related U.S. Application Data

(60) Provisional application No. 61/406,429, filed on Oct. 25, 2010.

(51) Int. Cl.
| | | |
|---|---|---|
| *C12N 5/00* | (2006.01) | |
| *A61K 38/00* | (2006.01) | |
| *A61K 35/30* | (2015.01) | |
| *A61K 39/00* | (2006.01) | |
| *C12N 5/095* | (2010.01) | |
| *A61K 31/4375* | (2006.01) | |
| *A61K 31/495* | (2006.01) | |
| *A61K 31/573* | (2006.01) | |
| *A61K 45/06* | (2006.01) | |
| *C07K 16/18* | (2006.01) | |

(52) U.S. Cl.
CPC ............ *A61K 35/30* (2013.01); *A61K 31/4375* (2013.01); *A61K 31/495* (2013.01); *A61K 31/573* (2013.01); *A61K 39/0011* (2013.01); *A61K 45/06* (2013.01); *C07K 16/18* (2013.01); *C12N 5/0695* (2013.01); *A61K 2039/5152* (2013.01); *A61K 2039/5154* (2013.01); *A61K 2039/5158* (2013.01); *A61K 2039/55511* (2013.01); *C12N 2500/90* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Albert et al. |
| 4,559,157 | A | 12/1985 | Smith et al. |
| 4,608,392 | A | 8/1986 | Jacquet et al. |
| 4,816,567 | A | 3/1989 | Cabilly et al. |
| 4,820,508 | A | 4/1989 | Wortzman |
| 4,938,949 | A | 7/1990 | Borch et al. |
| 4,946,778 | A | 8/1990 | Ladner et al. |
| 4,992,478 | A | 2/1991 | Geria |
| 5,091,513 | A | 2/1992 | Huston et al. |
| 5,260,203 | A | 11/1993 | Ladner et al. |
| 5,455,030 | A | 10/1995 | Ladner et al. |

FOREIGN PATENT DOCUMENTS

| | | |
|---|---|---|
| EP | 0058481 A1 | 8/1982 |
| EP | 0133988 A2 | 3/1985 |
| EP | 0239400 A2 | 9/1987 |
| EP | 0404097 A2 | 6/1990 |
| WO | WO 92/01047 A1 | 1/1992 |
| WO | WO 92/03918 A1 | 3/1992 |
| WO | WO 92/20791 A1 | 11/1992 |
| WO | WO 93/06213 A1 | 4/1993 |
| WO | WO 93/11161 A1 | 6/1993 |
| WO | WO 93/11236 A1 | 6/1993 |
| WO | WO 93/12227 A1 | 6/1993 |
| WO | WO 94/02602 A1 | 6/1993 |
| WO | WO 93/19172 A1 | 9/1993 |
| WO | WO 94/25585 A1 | 11/1994 |
| WO | WO 95/01438 A1 | 1/1995 |
| WO | WO 95/15388 A1 | 6/1995 |
| WO | WO 96/2576 A1 | 2/1996 |
| WO | WO 96/33735 A1 | 10/1996 |
| WO | WO 96/34095 A1 | 10/1996 |

OTHER PUBLICATIONS

Adams et al., "Immunization of malignant melanoma patients with full-length NY-ESO-1 protein using TLR7 agonist Imiquimod as vaccine adjuvant", *J. Immunol.* 181, 776-784 (2008).
Altschul et al., "Basic Local Alignment Search Tool", *J. Mol. Biol.* 215, 403-410 (1990).
Ardon et al., "Integration of autologous dendritic cell-based immunotherapy in the primary treatment for patients with newly diagnosed glioblastoma multiforme: a pilot study", *J. Neurooncol.* 99, 261-272 (2010).
Bao et al., "Glioma stem cells promote radioresistance by preferential activation of the DNA damage response", *Nature* 444, 756-760 (2006).
Bauer et al., "Human TLR9 confers responsiveness to bact6erial DNA via species-specific CpG motif recognition", *Proc. Natl Acad Sci*, 98(16), 9237-9242 (2001).
Beachy et al., "Tissue repair and stem cell renewal in carcinogenesis", *Nature* 432, 324-331 (2004).
Beaucage et al., "Deoxynucleoside Phosphoramidites—A New Class of Key Intermediates for Deoxypolynucleotide Synthesis", *Tet. Let* 22(20), 1859-1862 (1981).

(Continued)

*Primary Examiner* — Michail Belyavskyi
(74) *Attorney, Agent, or Firm* — Viksnins Harris & Padys LLP

(57) ABSTRACT

The present invention is directed to compositions and methods for treating an animal diagnosed with Glioblastoma multiforme (GBM).

10 Claims, 8 Drawing Sheets

(56) References Cited

OTHER PUBLICATIONS

Beier et al., "CD133+ and CD133-Glioblastoma-Derived Cancer Stem Cells Show Differential Growth Characteristics and Molecular Profiles", *Cancer Research* 67, 4010-4015 (2007).
Bernstein et al., "Adjuvant effects of Imiquimod on a herpes simplex virus type w glycoprotein vaccine in guinea pigs", *J. Infect Dis.* 167, 731-735 (1993).
Better et al., "Expression of Engineered Antibodies and Antibody Fragments in Microorganisms", *Methods in Enzymology* 178, 476-496 (1989).
Bird et al., "Single Chain Antibody Variable Regions", *Tibtech* 9, 132-137 (1991).
Bonnet et al., "Human acute myeloid leukemia is organized as a hierarchy that originates from a primitive hematopoietic cell", *Nature Medicine* 3, 730-737 (1997).
Brennan et al., "Preparation of Bispecific Antibodies by Chemical Recombination of Monoclonal Immunoglobulin G1 Fragments", *Science* 229, 81-83 (1985).
Brodeur et al., "Mouse-Human Myeloma Partners for the Production of Heterohybridomas", Monoclonal Antibody Production Techniques and Application, pp. 51-63 (Marcel Dekker, Inc., New York, 1987).
Buatti et al., "Radiation therapy of pathologically confirmed newly diagnosed glioblastoma in adults", *J. Neurooncol*, 89, 313-337 (2008).
Carter et al., "High Level *Escherichia coli* Expression and Production of a Bivalent Humanized Antibody Fragment", *Bio/Technology* 10, 163-167 (1992).
Champe et al., "Monoclonal Antibodies that Block the Activity of Leukocyte Function-associated Antigen 1 Recognize Three Discrete Epitopes in the Inserted Domain of CD11a*", *J. Biol. Chem.* 270, 1388-1394 (1995).
Clackson et al., "Making antibody fragments using phage display libraries", *Nature* 352, 624-628 (1991).
Clinical Trial NCT01171469, University of Minnesota, "Vaccination with Dendritic Cells Loaded with Brain Tumor Stem Cells for Progressive Malignant Brain Tumor", www.clinicaltrials.gov/archive/NCT01171469/2010_07_2, 4 pages (2010).
Cobb et al., "Human cytomegalovirus infection and expression in human malignant glioma", *Cancer Res* 62, 3347-3350 (2002).
Coffman et al., "Vaccine Adjuvants: Putting Innate Immunity to Work", *Immunity* 33, 492-503 (2010).
Copier et al., "Cell based cancer vaccines: Regulatory and commercial development", *Vaccine* 25S, B35-B46 (2007).
Craft et al., "The TLR7 agonist Imiquimod enhances the anti-melanoma effects of a recombinant Listeria monocytogenes vaccine", *J. Immunol.* 175, 1983-1990 (2005).
DeFrancesco, "Landmark approval for Dendreon's cancer vaccine", *Nat Biotechnol* 28, 531-532 (2010).
De St. Groth et al., "Production of Monoclonal Antibodies: Strategy and Tactics", *J. Immunol. Methods*, 35, 1-21 (1980).
Edwards et al., "Toll-like receptor expression in murine DC subsets: lack of TLR7 expression by DC8α+ DC correlates with unresponsiveness to imidazoquinolines", *Eur. J Immunol* 33, 827-833 (2003).
Eramo et al., "Chemotherapy resistance of glioblastoma stem cells", *Cell Death and Differentiation* 13, 1238-1241 (2006).
Evans et al., "Hypoxia is important in the biology and aggression of human glial brain tumors", *Clin. Cancer Res* 10, 8177-8184 (2004).
Frazier et al., "Treatment of diffuse brainstem gliomas: failed approaches and future strategies", *J. Neurosurg Pediatrics* 3, 259-269 (2009).
Froehler et al., "Synthesis of DNA via deoxynucleoside-H-phosphonate intermediates", *Nucl. Acid. Res.* 14 (13), 5399-5407 (1986).
Gaffney et al., "Large-Scale Oligonucleotide Synthesis by the H-Phosphonate Method", *Tet. Let.* 29(22), 2619-2622 (1988).
Galfre et al., "Rat x rat hybrid myelomas and a monoclonal anti-Fd portion of mouse IgG", *Nature* 277, 131-133 (1979).
Galli et al, "Isolation and characterization of tumorigenic, stem-like neural precursors from human glioblastoma", *Cancer Research* 64, 7011-7021 (2004).
Garegg et al, "Nucleoside H-Phosphonates. III. Chemical Synthesis of Oligodeoxyribotrucleotides by the Hydrogenphosphonate Approach", *Tet. Let.* 27 (34), 4051-4054 (1986).
Garegg et al., "Nucleoside H-Phosphonates. IV. Automated Solid Phase Synthesis of Oligoribonticleotides by the Hydrogenphosphonate Approach", *Tet. Let.* 27 (34), 4055-4058 (1986).
Gasser et al.. "The DNA damage pathway regulates innate immune system ligands of the NKG2D receptor", *Nature* 436, 1186-1190(2005).
Gibson et al., "Plasmacytoid dendritic cells produce cytokines and mature in response to the TLR7 agonists, imiquimod and resiquimod", *Cell Immunol* 218, 74-86 (2002).
Gill et al., "Use of imiquimod 5% cream (Aldara™) in cats with multicentric squamous cell carcinoma in situ: 12 cases (2002-2005)*", *Vet Comp Oncol* 6, 55-64 (2008).
Gordan et al., "Hypoxia-inducible factors: central regulators of the tumor phenotype", *Curr Opin Genet Dev* 17, 71-77 (2007).
Green et al., "Antigen-specific human monoclonal antibodies from mice engineered with human lg heavy and light chain YACs", *Nat. Genet.* 7, 13-21 (1994).
Gunther et al., "Glioblastoma-derived stem cell-enriched cultures form distinct subgroups according to molecular and phenotypic criteria", *Oncogene* 27, 2897-2909 (2008).
Harrison et al., "Reduction of recurrent HSV disease using Imiquimod alone or combined with as glycoprotein vaccine", *Vaccine* 19, 1820-1826 (2001).
Hartmann et al., "Rational design of new CpG oligonucleotides that combine B cell activation with high IFN-α induction in plasmacytoid dendritic cells". *Eur. J. Immunol.* 33, 1633-1641 (2003).
Holliger et al., "'Diabodies': Small bivalent and bispecific antibody fragments", *Proc. Natl. Acad. Sci.* 90, 6444-6448 (1993).
Huston et al., "Protein engineering of antibody binding sites: Recovery of specific activity in an anti-digoxin single-chain FV analogue produced in *Escherichia coli*", *Proc. Natl. Acad. Sci.* 85, 5879-5883 (1988).
Ignatova et al., "Human cortical glial tumors contain neural stemlike cells expressing astroglial and neuronal markers in vitro", *Glia.* 39, 193-206 (2002).
Ingale et al., "Robust immune responses elicited by a fully synthetic three-component vaccine", *Nat Chem Biol.* 3 (10), 663-667 (2007).
Johnston et al., "Topical Imiquimod is a potent adjuvant to a weakly-immunogenic protein prototype vaccine", *Vaccine* 24, 1958-1965 (2006).
Jones et al., "Replacing the complementarity-determining regions in a human antibody with those from a mouse", *Nature* 321, 522-525 (1986).
Kantoff et al,, "Sipuleucel-T immunotherapy for castration-resistant prostate cancer", *N. Engl. J. Med* 363 (5), 411-422 (2010).
Karlin et al,, "Applications and statistics for multiple high-scoring segments in molecular sequences", *Proc. Natl. Acad. Sci.* 90, 5873-5877 (1993).
Kearney et al., "A new mouse myeloma cell line that has lost immunoglobulin expression but permits the construction of antibody-secreting hybrid cell lines", *J. Immunol.* 123 (4), 1548-1550 (1979).
Kohler et al., "Continuous cultures of fused cells secreting antibody of predefined specificity", *Nature* 256, 495-497 (1975).
Kohler et al., "Derivation of specific antibody-producing, tissue culture and tumor lines by cell fusion", *Eur. J. Immunol.* 6, 511-519 (1976).
Kozbar, "A Human Hybrid Myeloma for Production of Human Monoclonal Antibodies", *J. Immunol.* 133 (6), 3001-3005 (1984).
Krieg, "Therapeutic potential of Toll-like receptor 9 activation", *Nature Reviews Drug Discovery*, 5, 471-484 (2006).
Krishnamachari et al., "Innovative strategies for co-delivering antigens and CpG oligonucleotides", *Adv Drug Deliv Rev* 61, 205-217 (2009).

(56) References Cited

OTHER PUBLICATIONS

Krug et al., "Identification of CpG oligonucleotide sequences with high induction of IFN-α/β in plasmacytoid dendritic cells", *Eur. J. Immunol.* 31, 2154-2163 (2001).
Kunkel, "Rapid and efficient site-specific mutagenesis without phenotypic selection", *Proc. Natl. Acad. Sci.* 82, 488-492 (1985).
Lamoyi, "Preparation of F(ab')2 Fragments from Mouse IgG of Various Subclasses", *Methods in Enzymology* 121, 663-669 (1989).
Langer et al., "Biocompatibility of polymeric delivery systems for macromolecules", *J. Biomed. Mater. Res.* 15, 267-277 (1981).
Langer, "Controlled release of macromolecules", *Chem. Tech.* 12, 98-105 (1982).
Lapidot et al., "A cell initiating human acute myeloid leukaemia after transplantation into SCID mice", *Nature* 367, 645-648 (1994).
Le et al., "Cellular vaccine approaches", *Cancer J.* 16 (4), 304-310 (2010).
Lee et al., "Tumor stem cells derived from glioblastomas cultured in bFGF and EFG more closely mirror the phenotype and genotype of primary tumors than do serum-cultured cell lines", *Cancer Cell* 9, 391-403 (2006).
Li et al., "Isolation and characterization of brain tumor stem cells in human medulloblastoma", *Chinese Journal of Cancer*, 25(2), 241-246 (2006).
Li et al., "Hypoxia-inducible factors regulate tumorigenic capacity of glioma stem cells", *Cancer Cell* 15, 501-513 (2009).
Liau et al., "Treatment of a patient by vaccination with autologous dendritic cells pulsed with allogeneic major histocompatibility complex class I-matched tumor peptides", Case Report, *Neurosurg Focus* 9(6), 1-5 (2000).
Livak et al., "Analysis Gene Expression Data Using Real-Time Quantitative PCR and the 2- ΔΔCT Method", *Methods* vol. 25, 402-408 (2001).
Lonberg et al., "Antigen-specific human antibodies from mice comprising four distinct genetic modifications", *Nature* 368, 856-859 (1994).
Lu et al., "Treatment Failure of a TLR-7 Agonist Occurs Due to Self-Regulation of Acute Inflammation and can be Overcome by IL-10 Blockade", *J. Immunol* 184, 5360-5367 (2010).
Mailliard et al., "Alpha-type-1 polarized dendritic cells: a novel immunization tool with optimized CTL-inducing activity", *Cancer Res* 64, 5934-5937 (2004).
Margulies et al., "Somatic Cell Hybridization of Mouse Myeloma Cells", *Cell* 8, 405-415 (1976).
Marks et al., "By-passing Immunization, Human Antibodies from V-gene Libraries Displayed on Phage", *J. Mol. Biol* 222, 581-597 (1991).
Marks et al., "By-Passing Immunization: Building High Affinity Human Antibodies by Chain Shuffling", *Bio/Technology* 10, 779-783 (1992).
McCafferty et al., "Phage antibodies: filamentous phage displaying antibody variable domains", *Nature* 348, 552-554 (1990).
McCord et al., "Physiologic oxygen concentration enhances the stem-like properties of DC133+ human glioblastoma cells in vitro", *Mol Cancer Res* 7(4), 489-497 (2009).
McGhee et al., "New Perspectives in Mucosal Immunity with Emphasis on Vaccine Development", *Sem. Hematol.*, 30 (4) Suppl 4, 3-15 (1993).
Mendez et al., "Functional transplant of megabase human immunoglobulin loci recapitulates human antibody response in mice", *Nat. Genet.* 15, 146-156 (1997).
Milstein et al., "Preparation of Monoclonal Antibodies: Strategies and Procedures", *Methods Enzymol.* 73, 3-46 (1981).
Morimoto et al., "Single-step purification of F(ab')2 fragments of mouse monoclonal antibodies (immunoglobulins G1) by hydrophobic interaction high performance liquid chromatography using TSKgel Phenyl-5PW", *Journal of Biochemical and Biophysical Methods* 24, 107-117 (1992).
Morrison et al., "Chimeric human antibody molecules: Mouse antigen-binding domains with human constant region domains", *Proc. Natl. Acad. Sci.* 81, 6851-6855. (1984).

Nierkens et al., "In vivo Colocalization of Antigen and CpG within Dendritic Cells is Associated with the Efficacy of Cancer Immunotherapy", *Cancer Res* 68 (13), 5390-5396 (2008).
Okada et al., "Expression of glioma-associated antigens in pediatric brain stem and non-brain stem gliomas", *J Neuroonocol*, 88, 245-250 (2008).
Olin et al., "Gammadelta T-lymphocyte cytotoxic activity against Mycobacterium bovis analyzed by flow cytometry", *J. Immunol. Methods* 297, 1-11 (2005).
Olin et al., "Influence of Oxygen Concentration on Neurosphere Cultures Derived from Surgically Isolated Gliomas: implications for immunotherapy", Society of Neuro-oncology, Las Vegas, Nevada, Poster, Nov. 2008.
Olin et al., "Superior efficacy of tumor cell vaccines grown in physiological oxygen", *Clin. Cancer Res.*, vol. 16, 4800-4808 (2010).
Olin et al., "Oxygen is a Master Regulator of the Imunogenicity of Primary Human Glioma Cells", *Cancer Res* 71(21), 6583-6589 (2011).
Patent Cooperation Treaty, International Searching Authority, International Search Report and Written Opinion for PCT/US2011/057654, 18 pages, Jan. 2, 2012.
Pellegatta et al., "Neurospheres enriched in cancer stem-like cells are highly effective in eliciting a dendritic cell-mediated immune response against malignant gliomas", *Cancer Research* 66 (21), 10247-10252 (2006).
Platet et al., "Influence of oxygen tension on CD133 phenotype in human glimoa cell cultures". *Cancer Lett* 258, 286-290 (2007).
Pluckthun, "Antibodies from *Escherichia coli*", The Pharmacology of Monoclonal Antibodies, vol. 113, Chapter 11, eds. Rosenburge and Moore, Springer Verlag, N.Y., pp. 269-315 (1994).
Pollard et al., "Glioma Stem Cell Lines Expanded in Adherent Culture Have Tumor-Specific Phenotypes and are Suitable for Chemical and Genetic Screens", *Cell Stem Cell* 4, 568-580 (2009).
Pouyssegur et al., "Hypoxia signaling, in cancer and approaches to enforce tumour regression", *Nature* 441, 437-443 (2006).
Presta, "Antibody engineering", *Curr. Op. Struct. Biol.* vol. 2, 593-596 (1992).
Prins et al., "Autologous tumor-lysate pulsed dendritic cell vaccination, together with the TLR-7 agonist 5% imiquimod, and serum pro-inflammatory cytokine levels in glioblastoma patients", ASC Annual Meeting, Abstract No. 11021, 5 pages (2008). Citation: J. Clin Oncol, 26, 2008 (May 20 suppl; abstr 11021).
Ridgway, "The first 1000 dendritic cell vaccines", *Cancer Invest* 21, 873-886 (2003).
Riechmann et al., "Reshaping human antibodies for therapy", *Nature* 332 (24), 323-329 (1988).
Sampson et al., "Tumor-specific immunotherapy targeting the EGFRvIII mutation in patients with malignant glioma", *Semin Immunol.* 20, 267-275 (2008).
Sarver, "Toward understanding the informatics and statistical aspects of micro-RNA profiling", *J. Cardiovasc Transl. Res* 3, 204-211 (2010).
Sato et al., "Reshaping a Human Antibody to Inhibit the Interleukin 6-dependent Tumor Cell Growth", *Cancer Res.* 53, 851-856 (1993).
Sciandra et al., "Induction of glucose-regulated proteins during anaerobic exposure and of heat-shock proteins after reoxygenation", *Proc Natl Acad Sci* 81, 4843-4847 (1984).
Shulman et al., "A better cell line for making hybridomas secreting specific antibodies", *Nature* 276, 269-270 (1978).
Sidman et al., "Controlled Release of Macromolecules and Pharmaceuticals from Synthetic Polypeptides Based on Glutamic Acid", *Biopolymers* 22, 547-556 (1983).
Singh et al., "Identification of a cancer stem cell in human brain tumors", *Cancer Research* 63, 5821-5838 (2003).
Singh et al., "Identification of human brain tumour initiating cells", *Nature* 432, 396-401 (2004).
Takeshita et al., "Signal transduction pathways mediated by the interaction of CpG DNA with Toll-like receptor 9", *Semin. Immunol.* 16, 17-22 (2004).
Trowbridge, "Interspecidies Spleen-Myeloma Hybrid Producing Monoclonal Antibodies Against Mouse Lymphocyte Surface Glycoprotein, T200*", *J. Exp. Med.* 148, 313-323 (1978).

(56) References Cited

OTHER PUBLICATIONS

Tsuchida et al.,"Computed tomographic and histopathological studies of pontine glioma", *Child's Nerv. Syst.* 1, 223-229 (1985).

Unkeless, "Characterization of a Monoclonal Antibody Directed Against Mouse Macrophage and Lymphocyte Fc Receptors", *J. Exp. Med.* vol. 150, 580-596 (1979).

Van Den Brenk et al., "Production of metastases by a primary tumour irradiated under aerobic and anaerobic conditions in vivo", *Br J Cancer* 26, 402-412 (1972).

Van Gool et al., "Dendritic Cell Therapy of High-Grade Gliomas"*Brain Pathology*, 19, 694-712 (2009).

Verthelyi et al., "Differential signaling by CpG DNA in DCs and B cells: not just TLR9", *Trends Immunol.* 24 (10), 519-522 (2003).

Waterhouse et al., "Combinatoial infection and in vivo recombination: a strategy for making large phage antibody repertoires", Nucleic Acids Res. 21 (9), 2265-2266 (1993).

Wheeler et al., "Vaccination elicits correlated immune and clinical responses in glioblastoma multiforme patients", *Cancer Research*, 68 (14), 5955-5964 (2008).

Wikibooks, "Radiation Oncology/CNS/High grade glioma/Adjuvant therapy", http://en.wikibooks.org/w/index.php?title=Radiation_Oncology/CN, 15 pages (Jul. 12, 2011).

Wu et al., "Resiquimod: a new immune resorise modifier with potential as a vaccine adjuvant for Th1 immune responses", *Antiviral Res* 64, 79-83 (2004).

Wu et al., "Persistence of DC133+ cells in human and mouse glioma cell lines: detailed characterization of GL261 glioma cells with cancer stem cell-like properties", *Stem Cells Dev* 17, 173-178 (2008).

Yamanaka et al., "Vaccination of recurrent glioma patients with tumour lysate-pulsed dendritic cells elicits immune responses: results of a clinical phase I/II trial", *Br. J. Cancer* 89, 1172-1179 (2003).

Yamanaka et al., "Clinical evaluation of dendritic cell vaccination for patients with recurrent glioma results of a clinical phase I/II trial", *Clin Cancer Res.* 11, 4160-4167 (2005).

Yelton et al., "Fusion of mouse myeloma and spleen cells", *Lymphocyte Hybridomas* 81, 1-7 (1978).

Yu et al., "Vaccination with tumor lysate-pulsed dendritic cells elicits antigen-specific, cytotoxic T-cells in patients with malignant glioma", *Cancer Research* 64, 4973-4979 (2004).

Zeppernick et al., "Stem Cell Marker CD133 Affects Clinical Outcome in Glioma Patients", *Clin Cancer Res* 14 (1), 123-129 (2008).

Kefas et al., "MicroRNA-7 Inhibits the Epidermal Growth Factor Receptor and the Akt Pathway and is Down-Regulated in Glioblastoma", *Cancer Res.* 68 (10), (2008).

Zhu et al., "Identification of internalizing human single-chain antibodies targeting brain tumor sphere cells", Mol Cancer Ther 9(7), 2131-2141 (2010).

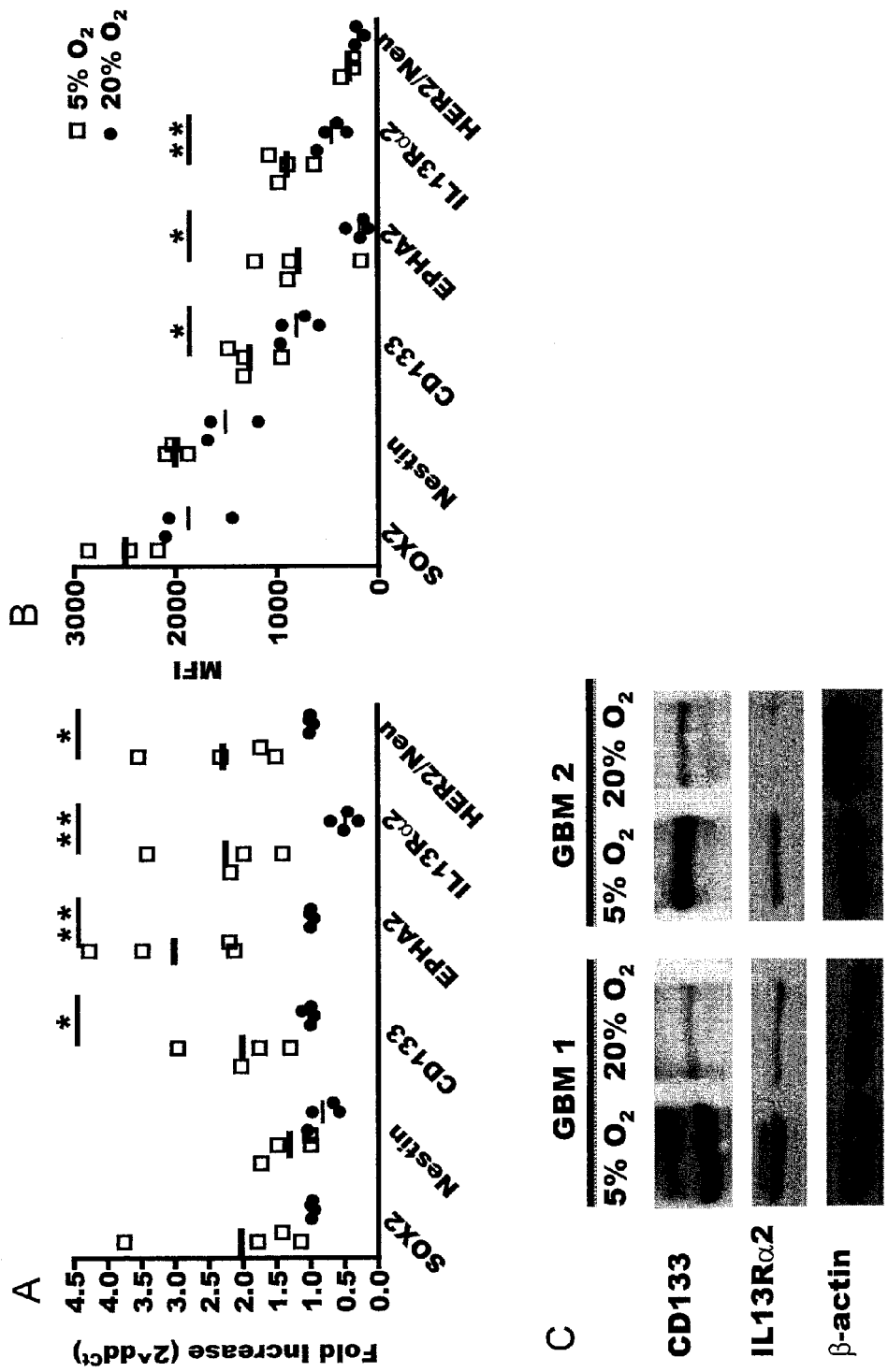
Fig. 6A-C

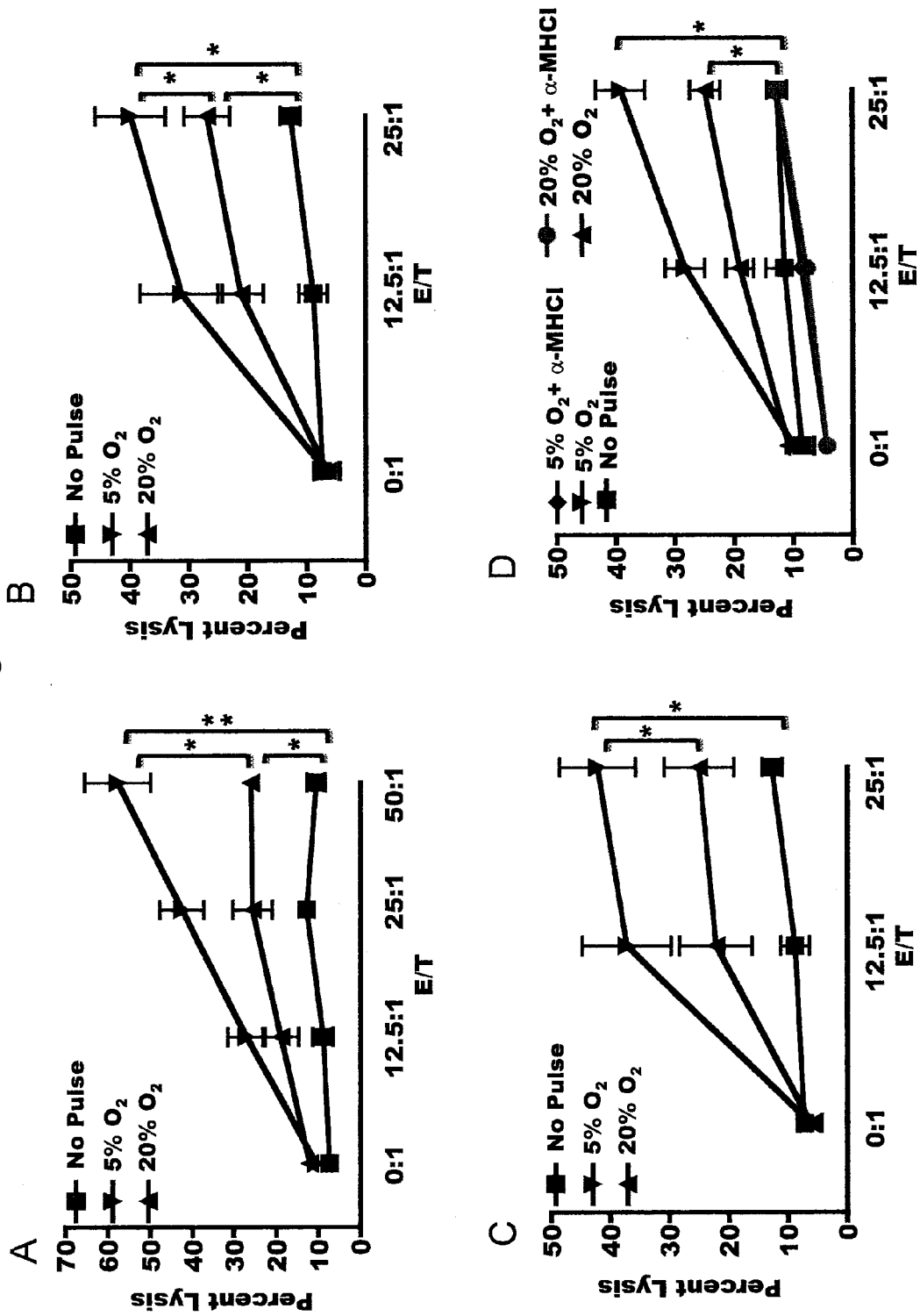
Fig. 7A-D

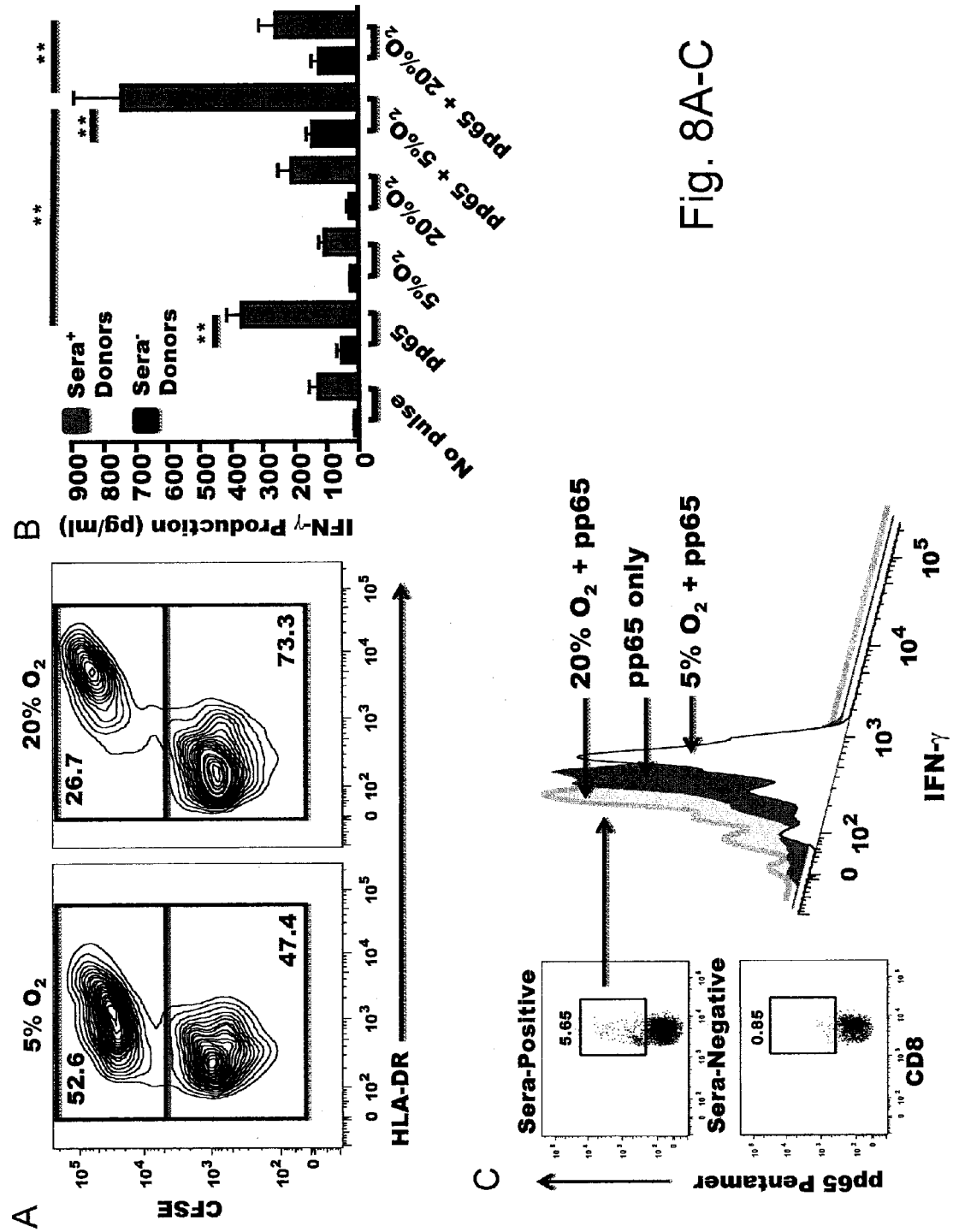
Fig. 8A-C

Fig. 9 Autologous Peripheral Blood-Derived DC Processing
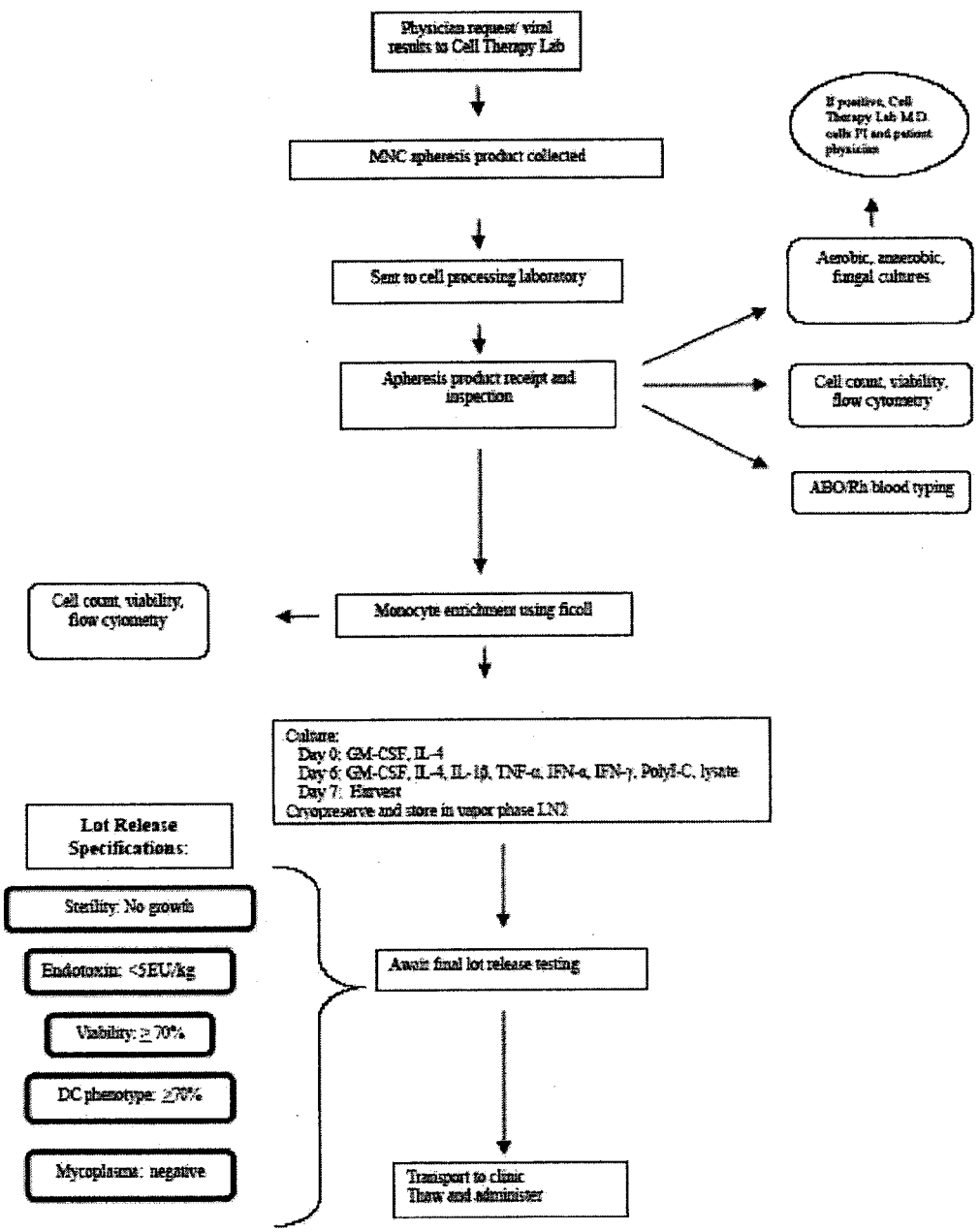

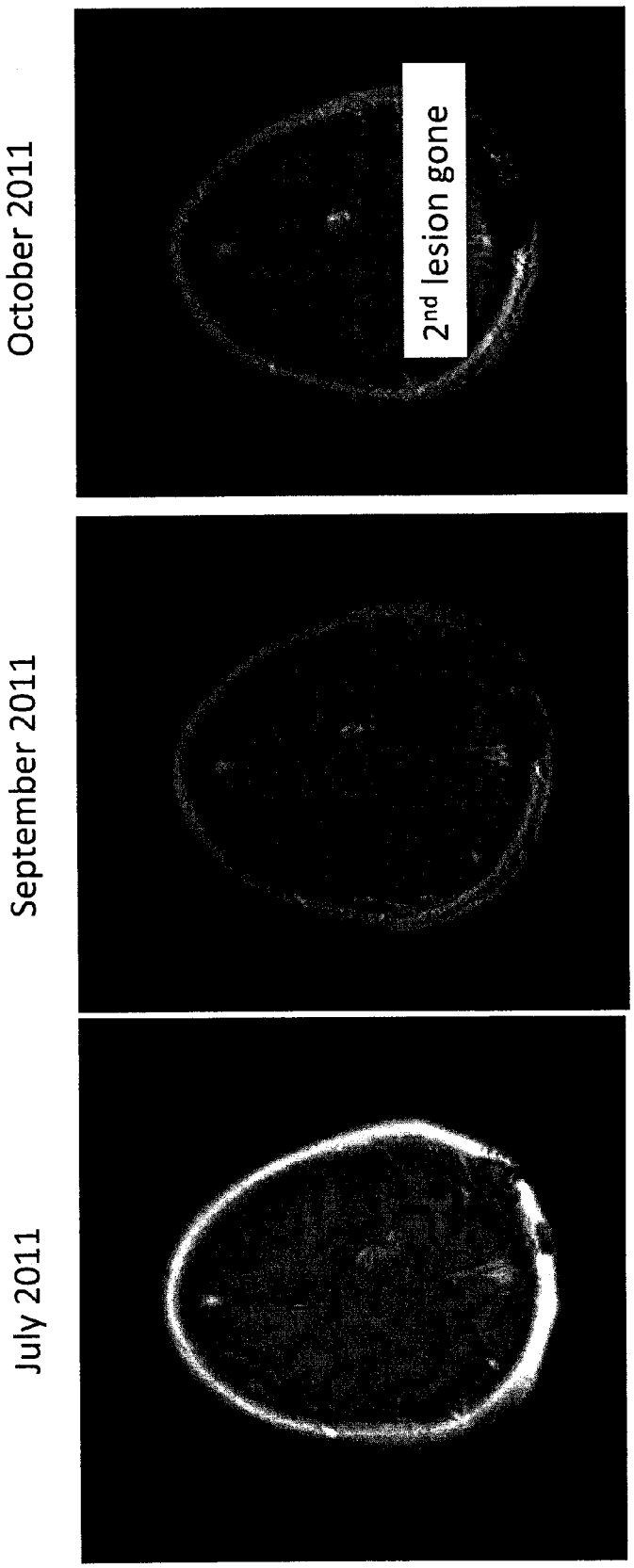
Fig. 10 Tumors Before and After

THERAPEUTIC COMPOSITION FOR TREATMENT OF GLIOBLASTOMA

CROSS-REFERENCE TO RELATED APPLICATIONS

This patent application claims the benefit of priority of U.S. application Ser. No. 61/406,429, filed Oct. 25, 2010, which application is herein incorporated by reference.

SEQUENCE LISTING

The instant application contains a Sequence Listing which has been submitted electronically in ASCII format and is hereby incorporated by reference in its entirety. Said ASCII copy, created on Feb. 25, 2016, is named 09531.305US1_SL.txt and is 3,707 bytes in size.

BACKGROUND OF THE INVENTION

Glioblastoma multiforme (GBM) is a common type of primary brain tumor in humans and is a very aggressive and devastating cancer, with a median survival of approximately one year. (Eramo et al., Chemotherapy resistance of glioblastoma stem cells, *Cell Death and Differentiation* (2006) 13, 1238-1241). Glioblastoma has the worst prognosis of any central nervous system malignancy. Therapy for GBM is difficult due to its biological location in the brain. Current treatments can involve chemotherapy, radiation, radiosurgery, corticosteroids, antiangiogenic therapy, and surgery. Despite the development of new surgical and radiation techniques and the use of multiple antineoplastic drugs, a cure for malignant gliomas does not exist. (Eramo et al., Chemotherapy resistance of glioblastoma stem cells, *Cell Death and Differentiation* (2006) 13, 1238-1241). Glioblastoma cells are resistant to cytotoxic agents, and the high incidence of recurrence in a very short period of time in glioblastoma patients suggests that tumorigenic cells are capable of overtaking the treatments.

SUMMARY OF THE INVENTION

The present invention provides an anti-tumor composition comprising a purified glioblastoma GBM6-AD stem cell. In certain embodiments, the cell is an adherent cell line in serum free media that is useful to generate anti-tumor immune responses. In certain embodiments, the present invention provides a glioblastoma stem cell line (GBM6-AD), assigned ATCC® Patent Deposit Designation PTA-11498. In certain embodiments, the GBM6-AD cells are lysed. In certain embodiments, the GBM6-AD cells are irradiated. In certain embodiments, the anti-tumor composition further comprises a physiologically-acceptable, non-toxic vehicle. In certain embodiments, the anti-tumor composition further comprises an adjuvant. In certain embodiments, the adjuvant is Imiquimod. In certain embodiments, the adjuvant is a toll-like receptor (TLR) ligand, such as CpG ODN, Annexin A2, Poly ICLC, or non-TLR ligands that stimulate immune responses. In certain embodiments, the composition is conjugated to a carrier such as a dendritic cell or a macrophage. In certain embodiments, the composition is contained in a non-cell carrier, such as a liposome.

The present invention provides a method of eliciting an immune response in an animal in need thereof, comprising administering to the animal the anti-tumor composition described above. In certain embodiments, the animal is a mammal, such as a human or non-human mammal. In certain embodiments, the method further comprises administering Imiquimod to the animal. In certain embodiments, the Imiquimod is administered prior to the administration of the anti-tumor composition. In certain embodiments, the anti-tumor composition is administered parenterally, such as intramuscularly, subcutaneously, intradermally or intravenously. Other modes of administration, however, such as oral or intranasal or delivery, are also acceptable. In certain embodiments, the anti-tumor composition is administered in more than one time point, such as in two time points. In certain embodiments, the anti-tumor composition is administered at a dose range of 1 µg-100 mg. GBM6-AD cells at each administration time point. In certain embodiments, the anti-tumor composition is administered at a dose of $2 \times 10^6$ GBM6-AD cells at each administration time point. In certain embodiments, the Imiquimod is administered topically. In certain embodiments, the Imiquimod is administered topically at two suprascapular injection sites.

In certain embodiments, the method further comprises administering irradiation therapy to the animal. In certain embodiments, the irradiation therapy is administered before, during or after administration of the anti-tumor composition. In certain embodiments, the irradiation therapy is administered at a dose of less that 6,000 cGY. In certain embodiments, the irradiation therapy is administered over multiple time points. In certain embodiments, the irradiation therapy is administered over three time points. In certain embodiments, the irradiation therapy is administered at a dose of 5220 cGY, followed by two additional doses of 360 cGY each. In certain embodiments, the first additional dose of 360 cGY is administered 10 weeks after the dose of 5220 cGY, and the second additional dose of 360 cGY is administered 14 weeks after the dose of 5220 cGY.

In certain embodiments, the method further comprises administering a radiation sensitizer temozolomide to the animal. In certain embodiments, the radiation sensitizer is a "parp inhibitor" (parp is a protein involved in DNA repair). In certain embodiments, the radiation sensitizer is temozolomide. In certain embodiments, the temozolomide is administered during initial radiation therapy. In certain embodiments, the temozolomide composition is administered at a dose range of 5-200 mg/m$^2$/day. In certain embodiments, the temozolomide is administered at a dose of 75 mg/m$^2$/day. In certain embodiments, the radiation therapy is at a dose of 5220 cGy in 180cGy fractions. In certain embodiments, the radiation therapy is administered over 6 to 7 weeks. In certain embodiments, the method further comprises administering additional 360 cGy fractions in 180cGy fractions over two consecutive days at 4 and 8 weeks following the initial radiation therapy.

In certain embodiments, the animal is a mammal, such as a human.

In certain embodiments, the method further comprises administering dexamethasone therapy to the animal. In certain embodiments, the dexamethasone therapy is administered at the time of diagnosis. In certain embodiments, the animal is weaned off dexamethasone by week 6 of initial radiation therapy.

In certain embodiments, the method further comprises administering a chemotherapy or drug that depletes regulatory T cell or myeloid derived suppressor cells. Examples include sunititib, ontak, cyclophosphamide, gemcitabine, retionoic acid.

The present invention provides a method of producing a dendritic cell vaccine, comprising pulsing dendritic cells with the anti-tumor composition described above.

The present invention provides a method of eliciting an immune response in an animal comprising introducing into the animal the composition described above.

The present invention provides a method of generating antibodies specific for GBM6-AD, comprising introducing into the animal the composition described above, and isolating antibodies specific for GBM6-AD.

The present invention provides a purified antibody that binds specifically to a purified adherent glioblastoma GBM6-AD stem cell, such a purified adherent glioblastoma GBM6-AD stem cell is ATCC® Patent Deposit Designation PTA-11498. In certain embodiments, the antibody is a human antibody or a humanized antibody. In certain embodiments, the antibody is a single-chain Fv or an scFv fragment.

The present invention provides a method of treating a primary brain tumor in a patient in need thereof, comprising administering to the patient the anti-tumor composition or purified antibodies that binds specifically to a purified adherent glioblastoma GBM6-AD stem cell as described above. In certain embodiments, the primary brain tumor is an astrocytoma, glioblastoma multiforme, medulloblastoma or ependymoma.

BRIEF DESCRIPTION OF THE FIGURES

FIGS. 6A-6C. Primary GBM cell lines cultured in 5% oxygen express high levels of glioma-associated and tumor-initiating proteins. A, cells from three gliomas cultured in 5% or 20% $O_2$ were analyzed for mRNA levels by real time PCR (n=4/group) and B, protein levels by flow cytometry (n=3-4/group). C, protein levels were validated by western analysis. *P<0.05; **P<0.01.

FIGS. 7A-7D. Brain TLs from 5% oxygen exhibit superior tumoricidal activity. PBMCs were stimulated with DCs pulsed with TL from 5% or 20% $O_2$ and incubated with A & B, HLA-A2 matched target glioblasomas or C, an ependymoma. D, to determine if the increased tumoricidal response was MHC-I-dependent, anti-ABC blocking antibody was added to target cells prior to PBMC. Data represent two separate experiments. Error bars, ±SEM. *P<0.05; **P<0.01.

FIGS. 8A-8C. Tumor lysates from 5% oxygen increase CD8 T cell priming Dendritic cells were pulsed with CFSE-labeled TLs derived in 5% or 20% $O_2$, stained with α-HLA-DR and A, analyzed by flow cytometry (representative of 3 replicates). $CMV^+$ PBMCs were co-cultured with DCs pulsed with 5% or 20% $O_2$ TLs+/−pp65 peptide for B, 48 h and analyzed for secreted IFNγ production, C, 72 h to determine $CD8^+pp65$ $pentamer^+$ IFNγ production on a per-cell basis. Error bars, ±SEM. *P<0.05; **P<0.01.

FIG. 9. Autologous peripheral blood-derived dc processing.

FIG. 10. Tumors before and after treatment. First panel at time=0, second panel shows the lesions after two months, and third panel shows lesions after three months. The second lesion is gone after three months.

DETAILED DESCRIPTION OF THE INVENTION

Anti-Tumor Compositions

Prior studies have shown that GBM is the most common histology of Diffuse Intrinsic Pontine Glioma (DIPG). Accordingly, it has been demonstrated that DIPG expresses GBM-associated immunogenic proteins that are currently being targeted in vaccine clinical trials including IL-13Rα2, Epha2, Her-2, and EGFRvIII (Wheeler C J, et al. Vaccination elicits correlated immune and clinical responses in glioblastoma multiforme patients. *Cancer Research.* 2008; 68:5955-5964; Okada H, et al. Expression of glioma-associated antigens in pediatric brain stem and non-brain stem gliomas. *J Neurooncol.* 2008; 88:245-250; Sampson J H, Archer, G. E., Mitchell, D. A., Heimberger, A. B. & Bigner, D. D. Tumor-specific immunotherapy targeting the EGFRvIII mutation in patients with malignant glioma. *Semin Immunol.* 2008; 20:267-275). However since DIPG is not a surgically accessible tumor, generation of cell lysate vaccines has been difficult. The present inventors have established a BTIC line, GBM6, grown in serum free stem cell media that can be used to treat DIPG with a lysate vaccine.

The inventors have also established a variant of the parent GBM6 line, named GBM6-AD that is adherent when grown in serum free stem cell media. As used herein the term "adherent cell line" means that the cell line grow as an adherent monolayer in completely serum free conditions (i.e., the cells are grown in culture, as monolayers on an artificial substrate (adherent culture) rather than free-floating in the culture medium (suspension culture)). As used herein, the term "adherent cell line" means that the cells are adherent in serum free stem cell media even on standard tissue culture flask (e.g., Falcon 75 $cm^2$ flask, 10 $cm^2$ dish, etc.) that are not treated with a reagent to make them adhere, such as fibronectin, matrigel, or laminin. Thus, the present cells adhere to a solid substrate even in the absence of the solid substrate being pre-treated. This is a very rare and unique property of this cell line. This feature allows for large scale cell manufacturing under clinical conditions much faster and much cheaper relative to cell lines that are non-adherent under serum free conditions.

GBM6-AD was more extensively passaged than GBM6 and over time its growth kinetics after thawing from liquid nitrogen increased. This is a significant advantage relative to GBM6 because it is possible to make much larger amounts of vaccine faster, which is an important consideration if the patient is rapidly dying. The GBM6 was also grown in 5% $O_2$ for an extended period of time to generate GBM6-AD, which seemed to make the cells become adherent, and importantly, more immunogenic.

Figure 1:
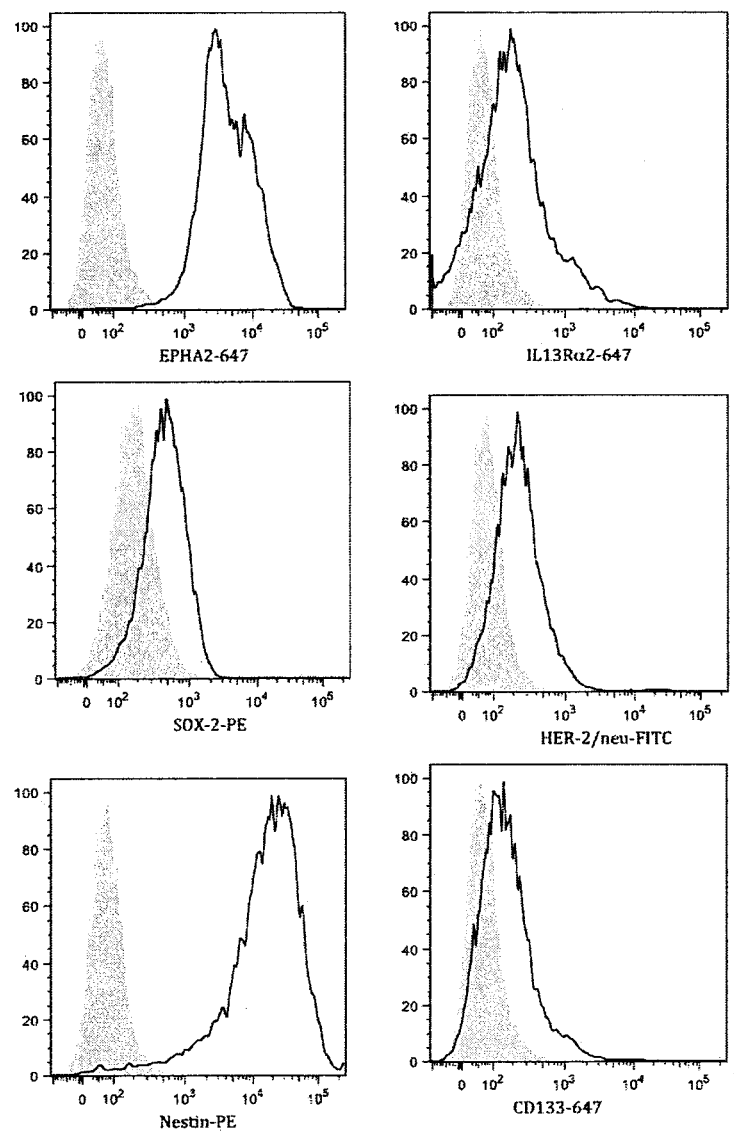
FIG. 1. Flow cytometry data of GBM6-AD cells to be used as a source of tumor antigen. Histograms show isotype staining to control for background binding (solid grey) and test antibody staining (white).

GBM6-AD was established under Good Manufacturing Practice (GMP) conditions at the University's Medical Center Clinical Cell Therapy Laboratory (FACT-accredited, CAP #18060-01, CLIA #24D0688128) in a class 10,000 production suite at the University's Molecular and Cellular Therapeutics (MCT) Facility. Flow cytometry data demonstrate that GBM6 expresses many important DIPG antigens including IL-13Rα2, Epha2, and Her-2 (FIG. 1). Moreover, GBM6-AD also expresses key BTIC antigens including CD133, nestin, and Sox-2 (FIG. 1). Based on this data, the vaccination of GBM6-AD lysate targets the majority of DIPGs and GBMs that do not occur in other parts of the brain.

The glioblastoma stem cell line GBM6-AD has been deposited with the American Type Culture Collection Depository (ATCC® Depository, 10801 University Boulevard, Manassas, Va. 20110-2209 USA) and assigned ATCC® Patent Deposit Designation PTA-11498. The cell line was deposited on Nov. 18, 2010. Access to this deposit will be available during the pendency of the application to the Commissioner of Patents and Trademarks and persons determined by the Commissioner to be entitled thereto upon request. The deposits will be maintained in the ATCC® Depository, which is a public depository, for a period of 30 years, or 5 years after the most recent request, or for the enforceable life of the patent, whichever is longer, and will be replaced if it becomes nonviable during that period.

In certain embodiments the GBM6-AD cells are manipulated, such as lysed or irradiated. Lysis can be achieved by methods including multiple freeze thaw cycles or using high pressure gas bubbles (nebulization) to "punch" holes in the cell. Lysates can be frozen quickly or using a control-rate freeze (e.g., 1 degree centigrade per minute) down to −80° C. or colder for storage. The cells can be irradiated prior generating a lysate, or the lysate itself can be irradiated to ensure complete cell death. Irradiation can be delivered from multiple devices including a cesium or cobalt irradiator.

Adjuvants

Vaccines commonly contain two components: antigen and adjuvant. The antigen is the molecular structure encoded by the pathogen or tumor against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered. Striking the right balance among these components is key to eliciting protective immunity.

1. Toll-Like Receptors

It has been estimated that most mammalian species have between ten and fifteen types of Toll-like receptors (TLRs). Eleven TLRs (named simply TLR1 to TLR11) have been identified in humans, and equivalent forms of many of these have been found in other mammalian species. TLRs function as a dimer Though most TLRs appear to function as homodimers, TLR2 forms heterodimers with TLR1 or TLR6, each dimer having different ligand specificity. The function of TLRs in all organisms appears to be similar enough to use a single model of action. Each Toll-like receptor forms either a homodimer or heterodimer in the recognition of a specific or set of specific molecular determinants present on microorganisms TLRs sense infection by recognizing pathogen associated molecular patterns and triggering inflammation. Therefore TLR ligands have been developed as vaccine adjuvants. In certain embodiments a ligand to TLR1 through TLR11 may be used as an adjuvant. The uptake of antigen and activation of TLR signaling by adjuvants are dynamic, extremely tenuous processes. Ideally, antigen-presenting cells (APC) that engulf antigen will also take up TLR ligand, resulting in up-regulation of co-stimulatory molecules, secretion of inflammatory cytokines, and presentation of antigen to T cells. This is certainly the case when APCs process viral particles, which contain both TLR ligands (e.g., dsRNA) and viral proteins. However, in the case of cancer vaccines the antigen and TLR ligand have been administered in mixture. This approach can result in several theoretical outcomes at the injection site: APCs that engulf antigen alone, TLR ligand alone, or TLR ligand with antigen (the desired outcome). Thus, co-administration can create a problem of signal to noise in the resulting immune response. Even when antigen and TLR ligand are engulfed by the same APC, the timing is critical. This was best demonstrated by Nierkens et al, who showed that uptake of TLR9 ligand prior to antigen significantly reduced cross presentation of antigen to CTLs relative to concurrent uptake (Nierkens S, et al., *Cancer Res.* 2008; 68:5390-5396). Accordingly, Ingale et al. have demonstrated that direct conjugation of TLR2 ligands to antigen by a covalent bond increased the titer of tumor-reactive IgG over 100,000 times relative to vaccination with a mixture of each component (Ingale S, et al., *Nat Chem Biol.* 2007; 3:663-667). Similarly, coupling antigen to TLR9 ligands increases the number of antigen-specific T cells 5 to 100 fold relative to co-administration of the two components separately (Krishnamachari Y, Salem A K. *Adv Drug Deliv Rev.* 2009; 61:205-217).

Imidazoquinoline is a double cyclic organic molecule that has been exploited as a vaccine adjuvant Imiquimod is an FDA-approved immune response modifier administered as a cream on the skin for the treatment of cutaneous tumors. Imiquimod exerts its immunostimulatory effects through TLR7 expressed on plasmacytoid dendritic cells and B cells in humans. Imiquimod treatment causes release of proinflammatory cytokines including interferonα, interferonγ, and IL-12, all of which are important for priming a robust $T_h1$ immune response associated with anti-tumor and anti-viral activity in animals. Topical Imiquimod has been used as a vaccine adjuvant with modest success in numerous studies targeting established tumors and viral infection. However the efficacy of Imiquimod is restrained by relying solely on TLR7 signaling because TLR7 is not expressed in one of the most abundant professional APCs, the CD8α$^+$TLR7$^-$ myeloid dendritic cells (Edwards A D, et al., *Eur J Immunol.* 2003; 33:827-833), thereby limiting efficacy. For this reason other compounds have been developed by modification of Imiquimod.

Resiquimod is a potent dual TLR7 and TLR8 ligand (Wu J J, et al., *Antiviral Res.* 2004; 64:79-83). Since TL 8 is expressed in CD8α$^+$ myeloid dendritic cells, it has overcome one of the limitations of Imiquimod (Coffman R L, et al., *Immunity;* 33:492-503). Nonetheless, many factors have limited the efficacy of resiquimod and Imiquimod. One recently identified mechanism for treatment failure is that although these drugs induce proinflamatory cytokines, they concurrently induce high levels of anti-inflammatory cytokines such as IL-10 (Gibson S J, et al., *Cell Immunol.* 2002; 218:74-86; and Lu H, et al., *J Immunol;* 184:5360-5367). Of clinical relevance, application of Imiquimod cream works on the treated tumor, but not distal tumors, suggesting an impairment in systemic immunity (Lu H, et al., *J Immunol;* 184: 5360-5367; and Gill V L, et al., *Vet Comp Oncol.* 2008; 6:55-64). Indeed blockade of IL-10 following Imiquimod treatment was shown to result in control of treated and distal (untreated) tumors, demonstrating the clinical significance of the self-regulating cytokine response induced by currently used Imidazoquinolines. Thus, a need exists to develop novel imquidazolequinoline-based compounds that trigger a more desirable ratio of pro- to anti-inflammatory cytokines. In certain embodiments of the present invention, a TLR-7 and/or TLR-8 (or combination TLR-7/8) molecule is administered.

Poly ICLC is an immunostimulant that consists of carboxymethylcellulose, polyinosinic-polycytidylic acid, and poly-L-lysine double-stranded RNA. It is a ligand for toll like receptor-3 (TLR3).

2. Annexin A2

Annexin A2 is a protein that in humans is encoded by the ANXA2 gene. Annexin 2 is involved in diverse cellular processes such as cell motility (especially that of the epithelial cells), linkage of membrane-associated protein complexes to the actin cytoskeleton, endocytosis, fibrinolysis, ion channel formation, and cell matrix interactions. It is a calcium-dependent phospholipid-binding protein whose function is to help organize exocytosis of intracellular proteins to the extracellular domain. Annexin 2A is a pleiotropic protein meaning that its function is dependent on place and time in the body.

3. Oligonucleotides

The term "nucleic acid" or "oligonucleotide" refers to a polymeric form of nucleotides at least five bases in length. The term "oligonucleotide" includes both single and double-stranded forms of nucleic acid. The nucleotides of the invention can be deoxyribonucleotides, ribonucleotides, or modified forms of either nucleotide. Generally, double-stranded molecules are more stable in vivo, although single-stranded molecules have increased activity when they contain a synthetic backbone.

An "oligodeoxyribonucleotide" (ODN) as used herein is a deoxyribonucleic acid sequence from about 3-1000 (or any integer in between) bases in length. In certain embodiments, the ODN is about 3 to about 50 bases in length. Lymphocyte ODN uptake is regulated by cell activation. For example, B-cells that take up CpG ODNs proliferate and secrete increased amounts of immunoglobulin. The present invention is based on the finding that certain oligonucleotides containing at least one unmethylated cytosine-guanine (CpG) dinucleotide activate the immune response.

A "CpG" or "CpG motif" refers to a nucleic acid having a cytosine followed by a guanine linked by a phosphate bond. The term "methylated CpG" refers to the methylation of the cytosine on the pyrimidine ring, usually occurring at the 5-position of the pyrimidine ring. The term "unmethylated CpG" refers to the absence of methylation of the cytosine on the pyrimidine ring. Methylation, partial removal, or removal of an unmethylated CpG motif in an oligonucleotide of the invention is believed to reduce its effect. Methylation or removal of all unmethylated CpG motifs in an oligonucleotide substantially reduces its effect. The effect of methylation or removal of a CpG motif is "substantial" if the effect is similar to that of an oligonucleotide that does not contain a CpG motif.

In certain embodiments the CpG oligonucleotide is in the range of about 8 to 1000 bases in size, or about 8 to 30 bases in size. For use in the present invention, the nucleic acids can be synthesized de novo using any of a number of procedures well known in the art. For example, the cyanoethyl phosphoramidite method (Beaucage, S. L., and Caruthers, M. H., Tet. Let. 22:1859, 1981); nucleoside H-phosphonate method (Garegg et al., Tet. Let. 27:4051-4054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated oligonucleotide synthesizers available in the market.

Alternatively, CpG dinucleotides can be produced on a large scale in plasmids, (see Sambrook, T., et al., Molecular Cloning: A Laboratory Manual, Cold Spring Harbor laboratory Press, New York, 1989), which after being administered to a subject, are degraded into oligonucleotides. Oligonucleotides can be prepared from existing nucleic acid sequences (e.g., genomic or cDNA) using known techniques, such as those employing restriction enzymes, exonucleases or endonucleases.

The CpG oligonucleotides of the invention are immunostimulatory molecules. An "immunostimulatory nucleic acid molecule" refers to a nucleic acid molecule, which contains an unmethylated cytosine, guanine dinucleotide sequence (i.e., "CpG DNA" or DNA containing a cytosine followed by guanosine and linked by a phosphate bond) and stimulates (e.g., has a mitogenic effect on, or induces or increases cytokine expression by) a dendritic cell. An immunostimulatory nucleic acid molecule can be double-stranded or single-stranded. Generally, double-stranded molecules are more stable in vivo, while single-stranded molecules have increased immune activity.

A "nucleic acid" or "DNA" means multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the term refers to ribonucleotides as well as oligodeoxyribonucleotides. The term shall also include polynucleosides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by oligonucleotide synthesis).

CpG ODNs

Three major classes of CpG ODN that are structurally and phenotypically distinct have been described. Examples of each class are shown in Krieg (Krieg, 2006, Nature Reviews Drug Discovery, 5, 471-484) together with the immune effects and structural characteristics that are specific to the class. The A-class CpG ODN (also referred to as type D) are potent inducers of interferon-α (IFNα) secretion (from plasmacytoid dendritic cells), but only weakly stimulate B cells. The structures of A-class ODN include poly-G motifs (three or more consecutive guanines) at the 5' and/or 3' ends that are capable of forming very stable but complex higher-ordered structures known as G-tetrads, and a central phosphodiester region containing one or more CpG motifs in a self-complementary palindrome. These motifs cause A-class ODN to self-assemble into nanoparticles. B-class ODN (also referred to as type K) have a phosphorothioate backbone, do not typically form higher-ordered structures, and are strong B-cell stimulators but weaker inducers of IFNα secretion. However, if B-class CpG ODN are artificially forced into higher-ordered structures on beads or microparticles, in dendrimers or with cationic lipid transfection, they exert the same immune profile as the A-class CpG ODN, thereby linking the formation of higher-ordered structures to biological activity. The C-class CpG ODN have immune properties intermediate between the A and B classes, inducing both B-cell activation and IFNα secretion. These properties seem to result from the unique structure of these ODN, with one or more 5' CpG motifs, and a 3' palindrome, which is thought to allow duplex formation within the endosomal environment (Krieg, 2006. Nature Reviews Drug Discovery, 5, 471-484; Takeshita F. et al., 2004. Semin Immunol. 16(1):17-22; Verthelyi D, Zeuner R A., 2003. Trends Immunol. 24:519-522).

CpG ODNs are synthetic oligonucleotides that contain unmethylated CpG dinucleotides in particular sequence contexts (CpG motifs). CpG motifs are present at a 20-fold greater frequency in bacterial DNA compared to mammalian DNA. They induce a coordinated set of immune responses based on the activation of immune cells primarily involved in the recognition of these molecules. Two types of CpG ODNs have been identified based on their distinct activity on plasmacytoid dendritic cells (PDC), key sensors of the CpG motifs (Krug A. et al., 2001. Eur J Immunol, 31(7): 2154-63). CpG-A is a potent inducer of IFN-α in plasmacytoid dendritic cells (PDC), whereas CpG-B is a weak inducer of IFN-α but a potent activator of B cells. Although the CpG motifs differ between mice and humans, in both species the recognition of CpG ODNs is mediated primarily by TLR9 (Bauer S. et al., 2001. Proc Natl Acad Sci USA, 98(16):9237-42).

A new type of CpG ODN has been recently identified, termed CpG-C, with both high induction of PDC and activation of B cells (Hartmann G. et al., 2003. Eur J Immunol. 33(6):1633-41). The sequence of CpG-C combines elements of both CpG-A and CpG-B. The most potent sequence is called M362, which contains a central palindromic sequence with CG dinucleotides, a characteristic feature of CpG-A, and a "TCGTCG motif" at the 5' end, present in CpG-B.

Formulations

In certain embodiments, anti-tumor composition formulations contain an effective amount of the purified glioblastoma GBM6-AD stem cells (the "active ingredient") in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required.

In certain embodiments, intranasal formulations include vehicles that neither cause irritation to the nasal mucosa nor significantly disturb ciliary function. Diluents such as water, aqueous saline or other known substances can be employed with the subject invention. In certain embodiments, the nasal formulations also contain preservatives such as, but not limited to, chlorobutanol and benzalkonium chloride. In certain embodiments, a surfactant is present to enhance absorption of the subject proteins by the nasal mucosa.

In certain embodiments, oral liquid preparations are in the form of, for example, aqueous or oily suspension, solutions, emulsions, syrups or elixirs, or are presented dry in tablet form or a product for reconstitution with water or other suitable vehicle before use. In certain embodiments, such liquid preparations contain conventional additives such as suspending agents, emulsifying agents, non-aqueous vehicles (which may include edible oils), or preservative.

In certain embodiments, to prepare an anti-tumor composition, the purified GBM6-AD, is isolated, lyophilized and/or stabilized, lysed as described above. The amount of GBM6-AD cells is then be adjusted to an appropriate concentration, optionally combined with a suitable adjuvant, and packaged for use. Suitable adjuvants include but are not limited to Imiquimod; surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of E. coli heat labile toxin or of the cholera toxin. McGhee, J. R., et al., "On vaccine development," Sem. Hematol., 30:3-15 (1993). Finally, the immunogenic product may be incorporated into liposomes for use in a formulation, or may be conjugated to proteins such as keyhole limpet hemocyanin (KLH) or human serum albumin (HSA) or other polymers.

In certain embodiments, the composition further contains one or more of the known TLR ligands. Specifically, in certain embodiments, the composition contains Annexin A2 (a protein) or fragments of Annexin A2 as a novel TLR2 ligand that is a great adjuvant. In certain embodiments, the TLR ligands are conjugated to proteins in the GBM-AD by covalent bonds. In certain embodiments, the TLR ligand is conjugated to a GBM6-AD protein by means of a malemide chemical linker.

Modes of Administration

The anti-tumor compositions, GBM6-AD derived vaccines, GBM6-AD reactive T cells and anti-GBM6-AD antibodies of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Methods of Treatment

Patients can be treated in a variety of ways, including the following:

Vaccine #1: Administration of apoptotic GBM6-AD cells (induced by irradiation and heatshock, so the cells are alive yet dying and all destined to die) by delivery into a subject with an appropriate adjuvant.

Vaccine #2: Administration of GBM6-AD cell lysates (induced by freeze thaw or nebulization) by delivery into a subject with an appropriate adjuvant.

Vaccine #3: Administration of Dendritic cells pulsed with apoptotic GBM6-AD cells (induced by irradiation and heat-shock, so the cells are alive yet dying and all destined to die) by delivery into a subject with an appropriate adjuvant.

Vaccine #4: Administration of dendritic cells pulsed with GBM6-AD cell lysates (induced by freeze thaw or nebulization) by delivery into a subject with an appropriate adjuvant.

Vaccine #5: Administration of dendritic cells fused to GBM6-AD with appropriate adjuvant (cell fusion vaccine).

Vaccine #6: Administration of B cells fused to GBM6-AD with appropriate adjuvant (cell fusion vaccine).

Vaccine #7: Administration of acid eluted peptides derived from the surface of GBM6-AD with appropriate adjuvant.

Vaccine #8: Any combination of one or more of the above.

In certain embodiments, the vaccine is injected intradermally or subcutaneous or intralymphnodally using doses and adjuvants as above for multiple cycles.

In certain embodiments, the patient is treated by means of adoptive cell therapy. In certain embodiments, the patients are administered T cells primed by GBM6-AD lysate-pulsed dendritic cells In certain embodiments, the patient is treated by the administration of antibodies specific for GBM6-AD antigens.

GBM6-AD Antibodies and GBM6-AD Reactive T Cells, and Methods of Making Anti-GBM6-AD Antibodies and GBM6-AD Reactive T Cells In certain embodiments, GBM6-AD reactive T cells are generated in culture by priming with autologous GBM6-AD pulsed dendritic cells and expansion using standard tissue culture methods and are administered to a patient. In sum, in certain embodiments, GBM6-AD is used directly as a vaccine, or is used indirectly to generate antibodies or T cells that are subsequently used as the direct therapy.

In certain embodiments, hybridomas are cloned that produce monoclonal antibodies against GBM6-AD. As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art. For example, the antibodies can be prepared by the methods described below.

GBM6-AD to be used for the immunization of animals includes lysed and irradiated GBM6-AD cells. As the antigen for immunization, the GBM6-AD cells can be used without modification, or after being conjugated with a carrier molecule. When a carrier molecule is used, for example, the GBM6-AD cell is first coupled with the carrier molecule, and then an adjuvant is added thereto. Such adjuvants include Alum, Freund's complete and incomplete adjuvants and the like, any of which can be combined together.

An antigen prepared as described above is given to a mammal, such as a mouse, rat, hamster, guinea pig, horse, monkey, rabbit, goat, and sheep. This immunization can be performed by any existing method, including typically used intravenous injections, subcutaneous injections, and intraperitoneal injections. There are no restrictions as to the immunization intervals. Immunization may be carried out at intervals of several days to several weeks, preferably four to 21 days. A mouse can be immunized, for example, at a single dose of 10 to 100 µg (for example, 20 to 40 µg) of the antigen protein, but the dose is not limited to these values.

Before the first immunization, and three to seven days after the second and subsequent immunizations, blood is collected from the animals, and the sera are analyzed for antibody titer. To promote an immune response, an aggregating agent such as alum is preferably used. In general, selected mammalian antibodies have sufficiently high antigen binding affinity.

Antibody affinity can be determined using a saturation binding assay, an enzyme-linked immunosorbent assay (ELISA), or a competitive assay (for example, radioimmunoassay).

Polyclonal antibodies can be screened by a conventional crosslinking analysis, such as that described in "Antibodies, A Laboratory Manual (Cold Spring Harbor Laboratories, Harlow and David Lane edit. (1988))." An alternative method is, for example, epitope mapping (Champe et al., J. Biol. Chem. 270:1388-1394 (1995)). A preferred method for determining polypeptide or antibody titers comprises quantifying antibody-binding affinity. In other embodiments, methods for assessing one or more biological properties of an antibody are also used in addition to or instead of the methods for determining antibody-binding affinity. Such analytical methods are particularly useful because they demonstrate the therapeutic effectiveness of antibodies. When an antibody exhibits an improved property in such analysis, its binding affinity is generally, but not always, enhanced.

Hybridomas that are used to prepare monoclonal antibodies can be obtained, for example, by the method of Milstein et al. (Kohler, G., and Milstein, C., Methods Enzymol. 1981, 73, 3-46). Myeloma cells to be fused with antibody-producing cells may be cell lines derived from any of the various animals, such as mice, rats, and humans, which are generally available to those skilled in the art. The cell lines to be used are drug-resistant, and cannot survive in a selective medium (e.g., HAT medium) in an unfused state, but can survive in a fused state. 8-azaguanine-resistant cell lines are generally used, which are deficient in hypoxanthine-guanine-phosphoribosyl transferase and cannot grow in a hypoxanthine-aminopterin-thymidine (HAT) medium. Myeloma cells include a variety of known cell lines, for example, P3x63Ag8.653 (J. Immunol. (1979) 123: 1548-1550), P3x63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), F0 (de St. Groth, S. F. et al., J. Immunol. Methods (1980) 35: 1-21), 5194 (Trowbridge, I. S., J. Exp. Med. (1978) 148: 313-323), R210 (Galfre, G. et al., Nature (1979) 277: 131-133), and P3U1 (J. Exp. Med. 1979, 150:580; Curr Top Microbiol. Immunol. 1978, 81:1). Human myeloma and mouse-human heteromycloma cell lines can also be used to produce human monoclonal antibodies (Kozbar, J. Immunol. 133:3001 (1984); Brodeur et al., Monoclonal Antibody Production Techniques and Application, pp. 51-63 (Marcel Dekker, Inc., New York, 1987)). Antibody-producing cells are collected, for example, from animals sacrificed two to three days after the final immunization. Antibody-producing cells include spleen cells, lymph node cells, and peripheral blood cells. Spleen cells are generally used. Specifically, tissues such as spleens or lymph nodes are excised or collected from the various animals described above. Then, the tissues are crushed and the resulting material is suspended in a medium or buffer, such as PBS, DMEM, or RPMI1640, followed by filtration with a stainless mesh or the like. This is then centrifuged to obtain antibody-producing cells of interest.

The above-described myeloma cells and antibody-producing cells are then fused. Cell fusion is achieved by contacting the myeloma cells with the antibody-producing cells at a ratio of 1:1 to 1:20 in a medium for animal cell culture, such as MEM, DMEM, and RPMI-1640, at 30 to 37° C. for one to 15 minutes in the presence of a fusion-promoting agent. To promote cell fusion, the antibody-producing cells and the myeloma cells may be fused using a commercially available cell-fusion device, using a fusion-promoting agent, such as polyethylene glycol (mean molecular weight 1,000 to 6,000 (Da)) or polyvinyl alcohol, or a virus for fusion, such as Sendai virus.

Hybridomas of interest are selected from the cells after cell fusion. The selection methods include methods using selective propagation of cells in a selective medium. Specifically, a cell suspension is diluted with an appropriate medium, and then the cells are plated on to microtiter plates. An aliquot of selection medium (for example, HAT medium) is added to each well, and then the cells are cultured while the selection medium is appropriately exchanged. The cells grown as a result can be saved as hybridomas.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

The antibodies of the present invention are antibodies that provide therapy for glioblastoma.

Methods for preparing monoclonal antibodies from the obtained hybridomas include standard cell culture methods and methods comprising ascites production. In cell culture methods, hybridomas are cultured for two to 14 days under standard culture conditions (for example, at 37° C. at 5% $CO_2$ atmosphere), in a culture medium for animal cells, such as RPMI-1640 or MEM containing 10 to 20% fetal calf serum, or serum-free medium, and antibodies are then prepared from the culture supernatant. In the method comprising ascites production, hybridomas are administered to the peritoneal cavities of mammalian individuals of the same species as that from which the myeloma cells are derived, and the hybridomas proliferate in to large quantities. Ascites or serum is then collected after one to four weeks. To enhance ascites production, for example, pristane (2,6,10,14-tetramethylpentadecane) may be pre-administered to the peritoneal cavity.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Examined Published Japanese Patent Application No. (JP-B) Hei 1-59878). Alternatively, the desired human antibody can also be obtained by using an antigen to immunize a transgenic (Tg) animal that comprises a partial or entire repertoire of human antibody genes (see Nature Genetics 7:13-21 (1994); Nature Genetics 15:146-156 (1997); Nature 368:856-859 (1994); International Patent Application WO 93/12227, WO 92/03918, WO 94/02602, WO 94/25585, WO 96/34096, and WO 96/33735). Specifically, such Tg animals are created as follows: a nonhuman mammal in which the loci of heavy and light chains of an endogenous immunoglobulin have been disrupted, and instead, the loci of heavy and light chains of a human immunoglobulin have been introduced via Yeast artificial chromosome (YAC) vectors and the like, is obtained by creating knockout animals or Tg animals, or mating such animals. The immunoglobulin heavy chain loci can be functionally inactivated, for example, by introducing a defect at a certain site in a J region or C region (e.g., Cµ region). The immunoglobulin light chains (e.g., κ chain) can be functionally inactivated, for example, by introducing a defect at a certain site in a J region or C region, or a region comprising the J and C regions.

Such a humanized antibody can also be obtained from culture supernatant, by using genetic engineering technology to transform eukaryotic cells with cDNAs that encode each of the heavy and light chains of the antibody, or preferably vectors comprising these cDNAs, and then culturing the transformed cells that produce the recombinant human monoclonal antibody. The hosts are, for example, desired eukaryotic cells, preferably mammalian cells, such as CHO cells, lymphocytes, and myelomas.

Furthermore, techniques to obtain human antibodies by panning with a human antibody library are known. For example, the variable region of a human antibody is expressed as a single chain antibody (scFv) on the surface of a phage, using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed, and then introduced into appropriate hosts and expressed to obtain human antibodies. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. The animal cells include: (1) mammalian cells such as CHO, COS, myeloma, baby hamster kidney (BHK), HeLa, and Vero cells; (2) amphibian cells such as Xenopus oocytes; or (3) insect cells such as sf9, sf21, and Tn5, or silkworms. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. The antibodies can be obtained by transferring the antibody genes of interest into these cells using transformation, and then culturing the transformed cells in vitro.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133, 988).

The antibodies of the present invention described above can be used in a treatment of an individual that has glioblastoma.

The following example is intended to illustrate but not limit the invention.

EXAMPLE 1

The present inventors have developed a novel therapy utilizing immunotherapy with Imiquimod and brain tumor initiating cell (BTIC) vaccine for the treatment of Diffuse Intrinsic Pontine Glioma (DIPG), a deadly brain tumor that occurs chiefly during childhood and the young adult years. The histology of the great majority of DIPGs is glioblastoma multiforme (GBM), WHO grade IV (Tsuchida T, Shimbo Y, Fukuda M, et al. Computed tomographic and histopathological studies of pontine glioma. *Child's Nery Syst.* 1985; 1:223-229). Past experience has shown that DIPG responds to radiation therapy, but only transiently. The majority of children afflicted with this tumor die within two years of diagnosis. Attempts to significantly improve outcomes with adjuvant chemotherapy and/or concurrent radio-sensitizing agents have failed to date (Frazier J L, Lee J, Ulrich W T, et al. Treatment of diffuse brainstem gliomas: failed approaches and future strategies. *J Neurosurg Pediatrics.* 2009; 3:259-269). Based on statistics from The Central Brain Tumor Registry of the United States (CBTRUS), the annual incidence of brain stem tumors in the 0 to 19 year-old age group is expected to be over 450 in the coming years. Of these, over 360 will be children and young adults with malignant DIPGs (Central Brain tumor registry of the United States. Retrieved 2009 Jul. 16, from Reports and Tables web site: http://cbtrus.org/reports/2009-NPCR-04-05/CBTRUS-NPCR2004-2005-Report-.pdf.2009). Few of these young people are expected to survive. This therapy results in increased survival among the young people afflicted with this disease.

The discovery that dendritic cells (DCs) play a pivotal role in antigen presentation and evoking adaptive immune responses has opened the possibility of manipulating them to treat GBM. Liau et al. published the first use of tumor peptide pulsed DC vaccination for a glioma patient in 2000; this study documented tumor-reactive T cells despite disease progression (Liau L M, et al. Treatment of a patient by vaccination with autologous dendritic cells pulsed with allogeneic major histocompatibility complex class I-matched tumor peptides. Case Report. Neurosurg Focus. 2000; 9:e8). Since then, vaccination of GBM patients with tumor lysate-pulsed autologous DC was able to elicit antigen-specific $CD8^+$ T cells and increase median survival to 133 weeks compared to 30 weeks in historical control patients receiving standard therapy (Yu J S, et al. Vaccination with tumor lysate-pulsed dendritic cells elicits antigen-specific, cytotoxic T-cells in patients with malignant glioma. *Cancer Research.* 2004; 64:4973-4979). Yamanaka et al. reported similar results in a phase I/II clinical trial following subdermal injection of tumor lysate-pulsed DCs or concurrent intratumoral and subdermal vaccination.

Four patients showed a clinical response, ten showed tumor stabilization, and ten had tumor progression (Yamanaka R, et al. Clinical evaluation of dendritic cell vaccination for patients with recurrent glioma: results of a clinical phase I/II trial. *Clin Cancer Res.* 2005; 11:4160-4167). In a recent phase II study, the ability of CTLs to elaborate IFN-γ in response to DC vaccinations was significantly correlated with clinical response and overall survival (Wheeler C J, et al. Vaccination elicits correlated immune and clinical responses in glioblastoma multiforme patients. *Cancer Research.* 2008; 68:5955-5964). Despite these promising results, most patients ultimately succumb to their disease. Immunotherapy will be more successful if specifically designed to target radiation resistant, brain tumor initiating cells.

Brain Tumor Initiating Cells: Markers and Implications for Immunotherapy

Research over the last 15 years suggests that heterogeneous populations of cells comprise a tumor, and only a subset of them is capable of self-renewal, tumor initiation, and partial differentiation (reviewed in Beachy P A, Karhadkar S S, Berman D M. Tissue repair and stem cell renewal in carcinogenesis. *Nature.* 2004; 432:324-331). The existence of tumor initiating cells was firmly established in the 1990s in acute mylogenous leukemia (Lapidot T, et al. A cell initiating human acute myeloid leukaemia after transplantation into SCID mice. *Nature.* 1994:367:645-648; Bonnet D, Dick J E. Human acute myeloid leukemia is organized as a hierarchy that originates from a primitive hematopoietic cell. Nature Medicine. 1997; 3:730-737) and very recently in primary brain tumors such as glioblastoma and medullablastoma (Ignatova T N, et al. Human cortical glial tumors contain neural stem-like cells expressing astroglial and neuronal markers in vitro. Glia. 2002; 39:193-206; Singh S K, et al. Identification of human brain tumour initiating cells. *Nature.* 2004; 432: 396-401; Singh S K, et al. Identification of a cancer stem cell in human brain tumors. *Cancer Research.* 2003; 63:5821-5828; Galli R, et al. Isolation and characterization of tumorigenic, stem-like neural precursors from human glioblastoma. *Cancer Research.* 20044:7011-7021; Li M C, et al. Isolation and characterization of brain tumor stem cells in human medulloblastoma. *Ai Zheng.* 2006; 25:241-246) is a 120-kDa transmembrane glycoprotein expressed in hematopoietic and neural stem cells that has been used as a marker for brain tumor initiating cells (BTIC). Singh et al. demonstrated that as few as 100 CD133$^+$ glioma cells were capable of tumor formation in immunodeficient mice, whereas 100,000 CD133$^-$ tumor cells isolated from the same bulk tumor mass engrafted but did not form tumors. (Singh S K, et al. Identification of human brain tumour initiating cells. *Nature.* 2004; 432:396-401). Moreover, the percentage of CD133$^+$ cells in the tumor mass increased in recurrent patients, and CD133 expression has now been used in predicting disease progression in low-grade gliomas (Zeppernick F, et al. Stem Cell Marker CD133 Affects Clinical Outcome in Glioma Patients. *Clin Cancer Res.* 2008; 14:123-129). However CD133 is not the only marker for BTICs since CD133$^-$ cells from a subset of gliomas are tumor initiating (Beier D, et al. CD133+ and CD133− Glioblastoma-Derived Cancer Stem Cells Show Differential Growth Characteristics and Molecular Profiles. *Cancer Research.* 2007; 67:4010-4015). Lee et al. have identified nestin$^+$Sox-2$^+$ cells isolated from human GBM that meet important criteria for BTIC (tumor initiation at low cell number) (Lee J, et al. Tumor stem cells derived from glioblastomas cultured in bFGF and EGF more closely mirror the phenotype and genotype of primary tumors than do serum-cultured cell lines. *Cancer Cell.* 2006; 9:391-403). These CD15$^+$ BTICs formed very invasive tumors upon transplantation into mouse brain and their gene expression signature closely resembled that of the primary tumor (Lee J, et al. Tumor stem cells derived from glioblastomas cultured in bFGF and EGF more closely mirror the phenotype and genotype of primary tumors than do serum-cultured cell lines. *Cancer Cell.* 2006; 9:391-403). Although CD133 and Sox-2 are useful markers, they cannot by themselves always predict tumor initiation. Nevertheless, cells expressing CD133 in particular seem to preferentially survive radiation and chemotherapy, making targeting them by immunotherapy very important. The key concept emerging from this research is that brain tumors are comprised of bulk tumor cells with limited tumorogenic potential and BTICs. BTICs may only account for a fraction of total tumor cells, but are the likely source of unrelenting tumor-renewal and disease progression.

Rationale for Using Radiation as a Vaccine Sensitizer.

Bao et al. have shown that CD133$^+$ cells exhibit enhanced resistance to ionizing radiation relative to their CD133$^-$ daughter cells by preferential activation checkpoint kinases Chk1, Chk2 (Bao S, et al. Glioma stem cells promote radioresistance by preferential activation of the DNA damage response. *Nature.* 2006; 444:756-760). Although CD133$^+$ and CD133$^-$ cells exhibited similar DNA damage, CD133$^+$ cells repaired the damage more rapidly and were enriched after each dose of radiation relative to CD133$^-$ cells (Bao S, et al. Glioma stem cells promote radioresistance by preferential activation of the DNA damage response. *Nature.* 2006; 444:756-760). In an elegant study, Gasser et al. demonstrated that the DNA damage pathway regulates innate immune system ligands of the NKG2D receptor (Gasser S, Orsulic, S., Brown, E. J. & Raulet, D. H. The DNA damage pathway regulates innate immune system ligands of the NKG2D receptor. *Nature.* 2005; 436:1186-1190). They determined that the molecular basis for radiation-induced NKG2D ligand expression was induction of Chk1/2 activation. Moreover, pharmacological inhibition of Chk1 inhibited NKG2D ligand upregulation, clearly revealing that radiation increases cellular immunogenicity through the checkpoint kinase pathway. However, these studies were conducted using normal cells and sarcoma cells (Gasser S, Orsulic, S., Brown, E. J. & Raulet, D. H. The DNA damage pathway regulates innate immune system ligands of the NKG2D receptor. *Nature.* 2005; 436:1186-1190). Nonetheless, if these results apply to glioma cells, then the same pathway used by CD133$^+$ cells to survive radiation therapy (signaling through Chk1) is expected to preferentially sensitize them to Natural killer or T cell cell-mediated lysis by upregulation of NKG2D ligands. If true, this would represent an "Achilles heel" for CD133$^+$ cells, which is defined as "a fatal weakness in spite of overall strength, actually or potentially leading to downfall." In certain embodiments, the present invention uses the combination of radiation with BTIC-targeted immunotherapy for treating DIPG.

Targeting BTIC Antigens: Culture Conditions of Glioma Cells have Crucial Implications for Immunotherapy.

For decades, research done to understand glioma biology and investigate potential therapies has relied on using glioma cell lines cultured in serum. Accordingly, in recent clinical trials where GBM patients were vaccinated with tumor cell lysate or peptide-pulsed DCs, the tumor cells were cultured and expanded in serum (Yu J S, et al. Vaccination with tumor lysate-pulsed dendritic cells elicits antigen-specific, cytotoxic T-cells in patients with malignant glioma. *Cancer Research.* 2004; 64:4973-4979; Yamanaka R, et al. Clinical evaluation of dendritic cell vaccination for patients with recurrent glioma: results of a clinical phase I/II trial. *Clin Cancer Res.* 2005; 11:4160-4167; Yamanaka R, et al. Vaccination of recurrent glioma patients with tumour lysate-pulsed dendritic cells elicits immune responses: results of a clinical phase I/II trial. *Br J Cancer.* 2003; 89:1172-1179). Two well controlled studies have recently shown that culture of BTICs in serum causes differentiation, leading to enhanced genomic instability, accelerating genetic mutation and leading to global gene expression patterns and phenotypes that are drastically different from the primary tumor (Lee J, et al. Tumor stem cells derived from glioblastomas cultured in bFGF and EGF more closely mirror the phenotype and genotype of primary tumors than do serum-cultured cell lines. *Cancer Cell.* 2006; 9:391-403; Gunther H S, et al. Glioblastoma-derived stem cell-enriched cultures form distinct subgroups according to molecular and phenotypic criteria. *Oncogene.* 2007). In contrast, culture of the primary tumor cells in neural stem cell media supplemented with EGF and FGF prevents differentiation. These neurosphere cultures recapitulate the genotype, gene expression pattern, and phenotype of the primary tumor when xenografted into mouse brain (Lee J, et al. Tumor stem cells derived from glioblastomas cultured in bFGF and EGF more closely mirror the phenotype and genotype of primary tumors than do serum-cultured cell lines. *Cancer Cell.* 2006; 9:391-403; Gunther H S, et al. Glioblastoma-derived stem cell-enriched cultures form distinct subgroups according to molecular and phenotypic criteria. *Oncogene.* 2007). One should consider these recent findings as attempts are made to develop more effective immunotherapy. When DCs are pulsed with a tumor lysate and administered as a vaccine, the protein antigens in the lysate are processed within the DC and presented on MHC I and MHC II to prime naïve T cells that respond to such antigens. Therefore, it is likely that until now, lysate pulsed DC vaccines have been biased to targeting only a subset of antigens expressed on the primary tumor, and probably few (if any) of these were BTIC-specific antigens since the antigen source was cultured in serum. One study has now provided evidence that supports this hypothesis. Pellegata et al. have shown that mice vaccinated with DCs pulsed with neurosphere-cultured lysate had superior therapeutic response compared to mice vaccinated with DCs pulsed with serum cultured glioma cell lysate (Pellegatta S, et al. Neurospheres enriched in cancer stem-like cells are highly effective in eliciting a dendritic cell-mediated immune response against malignant gliomas. *Cancer Research.* 2006; 66:10247-10252). In other words, the way DC vaccine trials have been conducted may create a problem of signal to noise. In the current project glioma cell cultures were derived from primary tumor and cultured in neural stem cell media to enrich for clinically relevant phenotype and expression of important BTIC antigens.

Imiquimod Plus Tumor Cell Lysate is a Potent Anti-Glioma Vaccine

Figure 2:
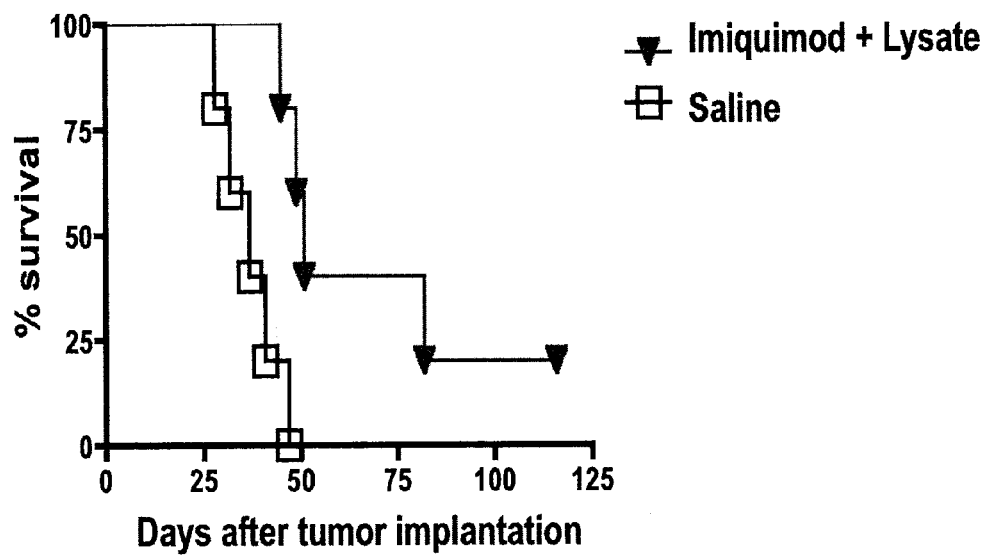
FIG. 2. Imiquimod/tumor lysate vaccine extends survival in murine GBM. C57BL/6 mice were implanted with GL261 glioma cells into the right striatum. Vaccination with GL261 lysate was administered by intradermal injection on days 3, 10, 17, 24, and 31 after tumor challenge Imiquimod cream was applied to skin covering the vaccination site each time. Saline treated mice were used as controls (N=5/group). Survival was significantly prolonged in the vaccinated group (Log-rank; p=00.06).

Imiquimod is an FDA-approved immune response modifier administered as a cream on the skin for the treatment of cutaneous tumors. Imiquimod exerts its immunostimulatory effects through toll-like-receptor 7 (TLR7) expressed on DCs and B cells in humans. Imiquimod treatment causes release of proinflammatory cytokines including interferonα, interferonγ, IL-12, all important for priming a robust Th1 immune response associated with anti-tumor activity in animals. Topical Imiquimod has been used as a vaccine adjuvant with success in numerous studies targeting established tumors and viral infection (Adams S, et al. Immunization of malignant melanoma patients with full-length NY-ESO-1 protein using TLR7 agonist Imiquimod as vaccine adjuvant. *J Immunol.* 2008; 181:776-784; Johnston D, Bystryn J C. Topical Imiquimod is a potent adjuvant to a weakly-immunogenic protein prototype vaccine. *Vaccine.* 2006; 24:1958-1965; Craft N, et al. The TLR7 agonist Imiquimod enhances the anti-melanoma effects of a recombinant *Listeria monocytogenes* vaccine. *J Immunol.* 2005; 175:1983-1990; Harrison C J, Miller R L, Bernstein D I. Reduction of recurrent HSV disease using Imiquimod alone or combined with a glycoprotein vaccine. *Vaccine.* 2001; 19:1820-1826; Bernstein D I, Miller R L, Harrison C J. Adjuvant effects of Imiquimod on a herpes simplex virus type 2 glycoprotein vaccine in guinea pigs. *J Infect Dis.* 1993; 167:731-735). Based on this previous work, the efficacy of a tumor cell lysate vaccine in a murine model as tested. Inbred C57BL/6 mice bearing syngeneic GL261 gliomas were treated by intradermal vaccinations with GL261 cell lysates whereby Imiquimod was applied to the vaccination site immediately before injection. Saline was administered as a control. Mice treated with Imiquimod/tumor lysate vaccination survival significantly longer than controls, including 20% long-term survival (FIG. 2; p<0.01).

Treatment Schema.

Figure 3:
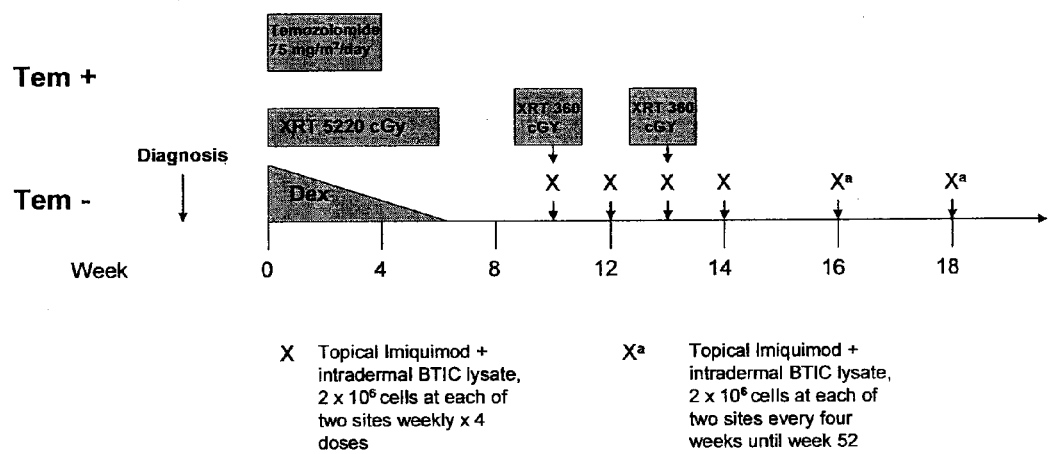
FIG. 3. Treatment schema. Half of patients receive temozolomide (tem+) and half do not (tem−) during the first four weeks of radiation therapy (XRT). Radiation is given in 180 cGy fractions. Imiquimod/BTIC vaccine is administered every two weeks from weeks 10 to 14, then every four weeks from weeks 16 to 52.
Figure 4:
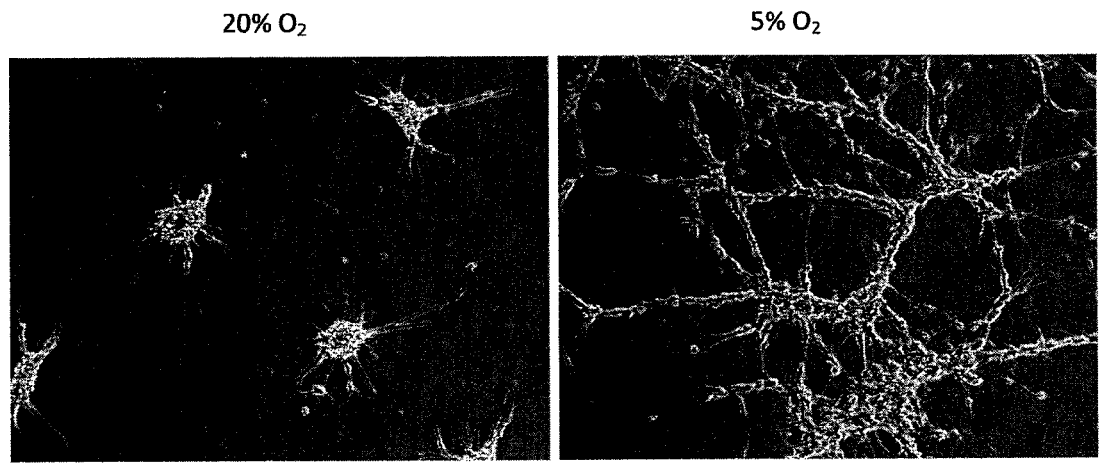
FIG. 4. Primary cells isolated from a human glioblastoma grown in two oxygen tensions. The identical number of glioma cells was seeded in complete stem cell media consisting of DMEM/F12, 20 ng/ml EGF and FGF, and 1× B27 and N2 supplement. Representative images were captured five days later.
Figure 5:
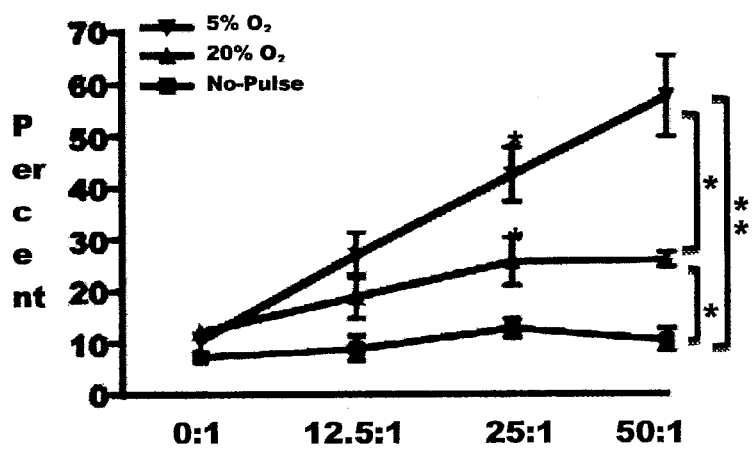
FIG. 5. This figure provides the results of GBM6 lysate-pulsed DCs primed tumoricidal T cells in tissue culture assay. This data directly shows GBM6 can generate tumoricidal immune responses.

The present treatment schema (FIG. 3) is based on the above data, and what is known about radiation increasing the immunogenicity of tumor cells. The BTIC cell line (GBM-6) is used as the vaccine source. Conformal radiation therapy to a dose of 5220 cGy in 180 cGy fractions is given over 6 to 7 weeks for induction in an attempt to achieve minimal residual disease. Additional 360 cGy fractions are delivered in 180 cGy fractions over two consecutive days at 4 and 8 weeks following the end of the initial radiation therapy in a novel effort to induce NKG2D ligand upregulation (thereby "sensitizing" residual tumor to lymphocyte attached). Therefore, the total radiation dose for each patient is 5940 cGy. Patients are assigned to two groups; temozolomide 75 mg/m$^2$/day is given to group 1 during the first four weeks of radiation therapy for adjuvant anti-tumor effect and radiosensitization. It is expected that temozolomide will cause lymphopenia. Vaccine is delivered during subsequent lymphocyte recovery in this group of patients in order to skew immune recovery towards T cells specific for tumor antigens expressed in DIPG such as IL-13Rα2, Epha2, Her-2. Recent data has shown that T regulatory cells may be the predominant lymphocyte subset that is delayed during temozolomide recovery, therefore, group 2 is treated with no adjuvant temozolomide. These patients may present to us upon referral from other institutions after initial radiation therapy has been completed. All other patients are randomly assigned to the temozolomide or no temozolomide arms. T reg numbers and immune response are compared between the two groups by flow cytometry on peripheral blood mononuclear cells collected before and after vaccine therapy initiates. Vaccine administration commences at week four following completion of radiation therapy and is given every two weeks for four doses. Subsequent every 4 week boosters are given and continue to a maximum of one year from initiation of radiation therapy, by which time median survival will have passed based on historical data.

Radiation therapy is given according to standard of care at the University of Minnesota Children's Hospital, with attention to the dosage guideline above. All patients are treated with Intensity Modulated Radiation Therapy (IMRT) or an equivalent conformal technique. The clinical target volume is defined as the gross tumor volume (full extent of tumor visible on MRI) plus 1 cm margin.

Most, if not all, patients will be placed on dexamethasone therapy at the time of diagnosis. An effort will be made to wean all patients off of dexamethasone by week 6 of initial radiation therapy, again to enable immune reconstitution prior to vaccine administration.

Administration of the vaccine is accomplished by first applying the Imiquimod topically at two suprascapular injection sites. The vaccine is then given intradermally in two divided doses approximating 2×10⁶ lysed, gamma irradiated GBM6-AD cells per dose at each administration time point.

EXAMPLE 2

Dendritic cell (DC) vaccination is a powerful approach for cancer immunotherapy that has recently obtained regulatory approval, and tumor lysate-pulsed DC vaccines are being tested in clinical trials. Tumor cell lysates (TLs) are often generated from cells cultured in atmospheric oxygen (~20% $O_2$), which is higher than the $O_2$ tension in the tumor in situ. It has been discovered that culturing murine tumor cells in 5% $O_2$ profoundly enhanced the efficacy of TL vaccines. The inventors thus sought to determine if culturing primary human glioma cells in 5% $O_2$ would enhance DC potency and tumor antigen expression. Unlike primary glioblastoma cells cultured in 20% $O_2$, cultures in 5% $O_2$ showed a partial reversion toward the gene expression patterns in the parental tumor in situ. Additionally, 5% $O_2$ TLs were taken up more efficiently by DCs, which exhibited a superior ability to present antigen to CD8 T cells. CD8 T cells primed by 5% $O_2$ lysate-pulsed DCs had significantly improved tumoricidal function relative to those primed by 20% $O_2$ TLs. Collectively the inventors' results demonstrate that tissue culture $O_2$ can: i) bias expression of target antigens to better reflect tumors in situ, ii) increase the potency of DCs for antigen presentation, iii) enhance effector function of CD8 T cells. These results have broad implications for improving the efficacy of TL-pulsed DC vaccines. Based on these data a clinical trial has been initiated using DCs pulsed with glioma cells expanded in 5% $O_2$ in serum-free conditions.

Therapeutic vaccination utilizing dendritic cells (DCs) pulsed with tumor-associated antigens is a promising approach for cancer immunotherapy (Ridgway D. The first 1000 dendritic cell vaccines. Cancer Invest 2003; 21: 873-86). The United States Food and Drug Administration recently approved a peptide-pulsed DC vaccine for the treatment of castration-resistant prostate cancer (DeFrancesco L. Landmark approval for Dendreon's cancer vaccine. Nat Biotechnol; 28: 531-2; Kantoff P W, Higano C S, Shore N D, et al. Sipuleucel-T immunotherapy for castration-resistant prostate cancer. N Engl J Med; 363: 411-22). Tumor cells are frequently used as a source of antigen for DC vaccines. Vaccines using tumor cells and tumor cell lysates (TLs) have several advantages including targeting multiple, patient-specific tumor antigens. Vaccination with TL-pulsed DCs has demonstrated encouraging results in early stage clinical trials in numerous malignancies, but there is clearly a need for additional improvements (Le D T, Pardoll D M, Jaffee E M. Cellular vaccine approaches. Cancer J; 16: 304-10).

It remains unclear how tissue culture might affect anti-tumor immune responses evoked by tumor cell vaccines. Primary glioblastoma cells cultured in serum-containing media were genetically and phenotypically very different from the primary tumor, whereas culture of the same cells in serum-free conditions more closely reflected the primary tumor and enriched for a cancer stem cell phenotype (Lee J, Kotliarova S, Kotliarov Y, et al. Tumor stem cells derived from glioblastomas cultured in bFGF and EGF more closely mirror the phenotype and genotype of primary tumors than do serum-cultured cell lines. Cancer Cell 2006; 9: 391-403). Glioma cell lysates generated in serum-free conditions were more effective than those derived from serum-containing media when employed for TL-pulsed DC vaccines in a murine model (Pellegatta S, Poliani P L, Como D, et al. Neurospheres enriched in cancer stem-like cells are highly effective in eliciting a dendritic cell-mediated immune response against malignant gliomas. Cancer Res 2006; 66: 10247-52). Traditionally, tumor cell vaccines are derived from cultures maintained at atmospheric oxygen (~20.95%; hereafter 20% $O_2$), far from the average oxygen tension of less than 6% $O_2$ measured in glioblastomas in situ (Evans S M, Judy K D, Dunphy I, et al. Hypoxia is important in the biology and aggression of human glial brain tumors. Clin Cancer Res 2004; 10: 8177-84). It is established that oxygen influences gene expression, cell metabolism, proliferation, survival (van den Brenk H A, Moore V, Sharpington C, Orton C. Production of metastases by a primary tumour irradiated under aerobic and anaerobic conditions in vivo. Br J Cancer 1972; 26: 402-12; Sciandra J J, Subjeck J R, Hughes C S. Induction of glucose-regulated proteins during anaerobic exposure and of heat-shock proteins after reoxygenation. Proc Natl Acad Sci USA 1984; 81: 4843-7; Pouyssegur J, Dayan F, Mazure N M. Hypoxia signalling in cancer and approaches to enforce tumour regression. Nature 2006; 441: 437-43; Gordan J D, Simon M C. Hypoxia-inducible factors: central regulators of the tumor phenotype. Curr Opin Genet Dev 2007; 17: 71-7), and hypoxia increases the expression of tumor stem cell markers CD133, Nestin, and SOX2 (Platet N, Liu S Y, Atifi M E, et al Influence of oxygen tension on CD133 phenotype in human glioma cell cultures. Cancer Lett 2007; 258: 286-90; McCord A M, Jamal M, Shankavaram U T, Lang F F, Camphausen K, Tofilon P J. Physiologic oxygen concentration enhances the stem-like properties of CD133+ human glioblastoma cells in vitro. Mol Cancer Res 2009; 7: 489-97; Li Z, Bao S, Wu Q, et al. Hypoxia-inducible factors regulate tumorigenic capacity of glioma stem cells. Cancer Cell 2009; 15: 501-13). However, the effect of oxygen on tumor cell immunogenicity is poorly understood.

The present results indicated that culturing primary glioma cells in 20% $O_2$ caused a global shift in gene expression away from the primary tumor, which was partially reversed by culturing cells at 5% $O_2$. Notably, expression of several glioma antigens known to elicit T cell responses was increased in 5% $O_2$. Primary human glioma cells grown in 5% $O_2$ exhibited intrinsic adjuvant properties as assessed by superior DC uptake, antigen presentation, and priming of tumoricidal CD8 T cells. Thus, primary human glioma cells grown in serum-free media at 5% $O_2$ emerge as the most recent improvement in the evolution of tumor cell vaccines.

Materials and Methods

Tumor cell culture: Surgically resected gliomas (Table 1) were enzymatically dissociated and cultured in neural stem cell media (Wu A, Oh S, Wiesner S M, et al. Persistence of CD133+ cells in human and mouse glioma cell lines: detailed characterization of GL261 glioma cells with cancer stem cell-like properties. Stem Cells Dev 2008; 17: 173-8).

TABLE 1

Table of the tumor identification, patient information, and the experiment in which the tumor was used, and passage number of the cells.

| Patient number | Id | Tumor | Experiment | Passage |
|---|---|---|---|---|
| Patient 1 | *BT130 | GBM | Microarray | 12 |
| Patient 2 | *BT132 | GBM | Microarray | 12 |

TABLE 1-continued

Table of the tumor identification, patient information, and the experiment in which the tumor was used, and passage number of the cells.

| Patient number | Id | Tumor | Experiment | Passage |
|---|---|---|---|---|
| Patient 3 | GBM6 | GBM | mRNA and Fc, CTL | 8 |
| Patient 4 | MNBT110 | GBM | mRNA, Fc, Westerns, CTL | 14 |
| Patient 5 | MNBT112 | Epd | CTL | 12 |
| Patient 6 | MNBT113 | GBM | mRNA, Fc Western | 14 |
| Patient 7 | MNBT 124 | GBM | mRNA, Fc | 15 |

*indicates that the tumor were resected at the Mayo Clinic, Rochester MN; others were resected University of Minnesota Medical Center, Fairview.
GBM = Glioblastoma multiforme,
Epd = Ependymoma,
FC = Flow Cytometry,
CTL = Cytotoxcity assay.

Unless explicitly stated, all tissue cultures were maintained at 20% $O_2$. Cultures labeled as "5% $O_2$" were converted from 20% $O_2$ cultures by maintenance at 5% $O_2$ for at least 30 days prior to use as described (Olin M R, Andersen B M, Zellmer D M, et al. Superior efficacy of tumor cell vaccines grown in physiologic oxygen. Clin Cancer Res; 16: 4800-8).

Microarray:

Total RNA was isolated from snap frozen tissue at resection, or cultured cells from either 5% or 20% $O_2$. Expression levels of 18,401 genes were analyzed using a Whole-Genome Gene Expression DASL Assay (Illumina, San Diego, Calif.).

Total RNA was isolated from snap frozen tissue at time of resection, and from cells grown in 5% and 20% $O_2$ using the RNEasy® Plus Mini Kit (Qiagen®, Valencia, Calif.) according to the manufacturer's instructions. Quality control was performed with an Agilent 2100 Bioanalyzer (Santa Clara, Calif.). Whole-Genome Gene Expression DASL Assay (Illumina, San Diego, Calif.) was used to analyze expression levels of 18,401 genes. Briefly, biotinylated cDNA was synthesized from 100 ng of total RNA from each sample using mixed poly-T and random nonamer primers. Biotinylated cDNA was hybridized to assay oligonucleotides, which were subsequently bound to streptavidin-conjugated paramagnetic particles. Oligos were extended and ligated, creating templates that were amplified with random, fluorescent primers. The fluorescently labeled products were bound to 24,631 oligonucleotide probes contained on each microarray of a Illumina HumanRef-8_V1 Expression BeadChip, and analyzed with laser confocal microscopy. Three technical replicates were analyzed for each condition for patient 2 and tissue from patient 1. Two technical replicates were performed for cell lines derived from patient 1.

Array data were analyzed for quality control as previously described (Sarver A L. Toward understanding the informatics and statistical aspects of micro-RNA profiling. J Cardiovasc Transl Res; 3: 204-11), quantile normalized, and multiple probes for each gene were averaged. For each set of experiments (tumor, 20% and 5% oxygen) each experimental value was divided by the average of the 20% $O_2$ culture to determine the differences between states independent of the differences between the different tumors. Two group t-tests as well as the average fold change were used to determine differentially expressed genes.

Quantitative RT-PCR:

Extracted RNA was analyzed by real time PCR using SYBR Green one step PCR master mix (Qiagen®). The following conditions were used for PCR in an ABI PRISM 7500 thermocycler: 95° C. for 15 min; 94° C. for 30s, 55° C. for 30s, 68° C. for 30s in a total of 40 cycles; 72° C. for 10 min; and 10° C. until collected. Relative quantification of gene expression was calculated and normalized to GAPDH expression levels using the $2^{-\Delta\Delta Ct}$ method (Livak K J, Schmittgen T D. Analysis of relative gene expression data using real-time quantitative PCR and the 2(-Delta Delta C(T)) Method. Methods 2001; 25: 402-8). Primers are listed in Table 2.

TABLE 2

List of primers used to determine transcription levels.

| Antigen | Primer Sequence |
|---|---|
| CD133 | Forward-5-TCG TAC TCG GCT CCC TGT TG-3 (SEQ ID NO: 1)<br>Reverse 5-ATT CAC GCG GCT GTA CCA CA-3 (SEQ ID NO: 2) |
| SOX2 | Forward 5-CCC CCG GCG GCA ATA GCA-3 (SEQ ID NO: 3)<br>Reverse 5-TCG GCG CCG GGG AGA TAC AT-3 (SEQ ID NO: 4) |
| NESTIN | Forward 5-AGG TAG AGG AGC TGG CAA GGC GAC-3 (SEQ ID NO: 5)<br>Reverse 5-TTT TCA GTA GCC CGC AGC CG-3 (SEQ ID NO: 6) |
| EPHA2 | Forward 5-CTG GCC TTC CAG GAT ATC GG-3 (SEQ ID NO: 7)<br>Reverse 5-TGC ACA GTG CAT ACG GGG CT-3 (SEQ ID NO: 8) |
| IL13Ra2 | Forward 5-CTG ATA AGC ACA ACA TTT GGC TCT-3 (SEQ ID NO: 9)<br>Reverse 5-TGA TGG TCT TCC ATG TTT CAC TAC C-3 (SEQ ID NO: 10) |
| HER2/Neu | Forward 5-CTG CAG CTT CGA AGC CTC ACA A-3 (SEQ ID NO: 11)<br>Reverse 5-ATG GCA GCA GTC AGT GGG CAG T-3 (SEQ ID NO: 12) |
| GAPDH | Forward 5-GTC GGA GTC AAC GGA TTT GGT-3 (SEQ ID NO: 13)<br>Reverse 5-GGG ATT TCC ATT GAT GAC AAG CT-3 (SEQ ID NO: 14) |

Flow Cytometry:

$5 \times 10^5$ cells were stained with: anti-CD133/2 (Miltenyi Biotec), EphA2, SOX2, Nestin, HER-2/neu (R&D Systems), and IL13Rα2 (SantaCruz Biotechnology). Following three washes, CD133/2 was stained with a secondary anti-mouse-647; IL13Rα2 and EphA2 were stained with secondary anti-mouse-PE along with their respective isotype and analyzed using a FACS Canto II. For DC phenotyping, $5 \times 10^5$ DCs were stained with CD80-FITC, CD86-PE, CD83-PE, HLA-DR-APC, CCR7-FITC (eBioscience) and HLA-ABC-FITC (BD Biosciences), incubated at 4° C. for 30 min, washed, fixed, then analyzed on a FACS Caliber. Intracellular staining was performed according to the manufacturer's protocol (BD Biosciences).

Dendritic Cells:

Monocytes were purified using CD14 magnetic beads (Miltenyi Biotech) from the peripheral blood of healthy HLA-A2$^+$ donors, plated at a concentration of $5 \times 10^5$ in 24-well plates and matured as previously described (Mailliard R B, Wankowicz-Kalinska A, Cai Q, et al. alpha-type-1 polarized dendritic cells: a novel immunization tool with optimized CTL-inducing activity. Cancer Res 2004; 64: 5934-7); on day 6, DCs were pulsed with 100 µg of TLs derived in either 5% or 20% $O_2$, and maturated prior to experiments.

CTL Assays:

1×10⁶ HLA-A2⁺ PBMCs from normal donors were added to matured (day 8) lysate-pulsed DCs with 50 U IL-2 and incubated seven days. For re-stimulation, a second set of pulsed DCs was added to the co-culture for four days. On day 11, primed PBMCs were co-cultured with 2×10⁴ CFSE-labeled HLA-A2⁺ glioma cells for 6 h, then analyzed by flow cytometry to determine cytotoxicity as described (Olin M R, Hwa Choi K, Lee J, Molitor T W. Gammadelta T-lymphocyte cytotoxic activity against *Mycobacterium bovis* analyzed by flow cytometry. J Immunol Methods 2005; 297: 1-11). For the blocking assay, anti-HLA-ABC was added to target cells for 25 min, washed, and added to effector cells.

CMV Assay:

5×10⁵ HLA-A2⁺ iDCs were pulsed with 100 µg of tumor lysates derived in 5% or 20% $O_2$+/−10 µg of pp65 HLA-A2-restricted CMV antigen (NLVPMVATV) (SEQ ID NO: 15) and matured as described in the methods section. Following maturation, DCs were washed 3 times, and 5×10⁵ PBMCs from CMV sera-positive donors were added to DCs. CMV sera-negative PBMCs were used as a negative control. Cells were incubated for 48 h, and supernatant was analyzed by cytometric bead array (BD Biosciences) for IFNγ. Cells were cultured for an additional 24 h, stained with anti-CD8, pp65 pentamer (ProImmune), and intracellularly stained for IFNγ production.

Increase in Tumoricidal Activity is not Due to an Increase in Co-Stimulatory Molecules.

To investigate if lysates derived in 5% $O_2$ culture altered co-stimulatory molecule expression, DCs were pulsed with tumor lysates derived in either 5% or 20% $O_2$ conditions, matured, and analyzed for CD83, CD80/86, HLA-DR, HLA-ABC, and CCR7 expression. In three separate experiments, no significant differences in co-stimulation markers were observed between the two oxygen conditions.

Statistical Analysis:

Statistical comparisons were made by ANOVA, followed by post hoc comparisons using a 2-tailed t-test. All tests were performed with Prism 4 software (Graph Pad Software, Inc). P values <0.05 were considered significant.

Results and Discussion

In order to compare tissue cultures to the primary tumor in situ, mRNA expression levels were profiled from two glioblastomas and cultured cells derived from the same tumor grown in 5% and 20% $O_2$. As a trend, the gene expression signature shifted towards the levels observed in situ when the cells were cultured in 5% $O_2$ relative to 20% $O_2$. There was a significant difference in the expression of 3,333 genes between the 20% $O_2$ culture and the in situ tumor in both patients. Of these, 77 genes were differentially expressed between the 5% and 20% $O_2$ cultures.

Selected cancer stem cell markers (CD133, Nestin, Sox2) and TAA known to elicit T cell responses (EphA2, IL-13Rα2, HER-2/neu) were analyzed by PCR and flow cytometry. Relative to 20% $O_2$, cells cultured in 5% $O_2$ expressed significantly more mRNA encoding for CD133, EphA2, IL-13Rα2 and HER-2/neu (FIG. 6A). SOX2 and Nestin demonstrated the same trend but failed to reach statistical significance. With the exception of HER-2/neu, protein expression followed the same trend with significant increases in CD133, EphA2, and IL13Rα2 (FIG. 6B). Moreover, western blot for CD133 and IL13Rα2 revealed similar changes in expression (FIG. 6C). Collectively, these experiments demonstrated that cells cultured in 5% $O_2$ better reflect the antigen expression on the tumor in situ and are enriched for markers of "stemness" and immunogenic TAA.

It was next asked if oxygen tension would alter the ability of TLs to prime tumoricidal T cells in culture. HLA-A2⁺ PBMCs from normal donors were primed by autologous DCs pulsed with TLs derived from three different glioma patients. Primed PBMCs were assessed for their ability to lyse the same HLA-A2⁺ glioma cells that were used for priming. PBMCs primed by 5% $O_2$ TLs demonstrated superior tumoricidal activity against target cells from 3/3 patients (FIG. 7A-C). To elucidate whether tumor cell lysis required priming CD8 T cells, an anti-HLA-ABC blocking antibody was added to tumor cells prior to effector cells. Blockade of MHC I-TCR interactions prevented a tumoricidal response, implicating cytotoxic T lymphocytes (CTLs) as the main effectors in this assay (FIG. 7D).

A plausible explanation for the enhancement in CTL priming would be improvement of DC maturation by 5% $O_2$ TLs. The expression of co-stimulatory molecules, MHC molecules, and CCR7 on mature DCs was measured after pulsing with TLs from 20% or 5% $O_2$. There were no significant differences in expression of CD83, CD80, CD86, or HLA-ABC, HLA-DR, or CCR7. Therefore, the adjuvant activity of 5% $O_2$ TLs was not likely due to enhancing DC maturation, suggesting other mechanisms. Experiments were conducted to determine whether the superior CTL priming achieved with 5% $O_2$ TLs could be due to changes in lysate uptake. Immature DCs were pulsed with TLs from CFSE-labeled glioma cells grown in 5% or 20% $O_2$. Flow cytometry-based detection of CFSE⁺HLA-DR⁺ cells (marking DCs loaded with lysate) revealed that 5% $O_2$ TLs were uptaken by twice the number of DCs compared to TLs derived in 20% $O_2$ (FIG. 8A). Thus, unidentified factor(s) in the 5% $O_2$ TLs increased the fraction of DCs that engulfed tumor-associated proteins in tissue culture.

The inventors established an assay to determine if TLs altered DC-mediated CD8 T cell priming from a defined antigen not present in the TLs. To accomplish this, TLs were mixed with pp65 peptide, a specific marker antigen with well-defined CD8 T cell responses. Cytomegalovirus (CMV)-derived pp65 is an HLA-A2-restricted immunodominant epitope to which CMV sera-positive patients typically have CD8 T cell memory responses (reviewed in (Moss P, Khan N. CD8(+) T-cell immunity to cytomegalovirus. Hum Immunol 2004; 65: 456-64)). PBMCs from sera-positive donors were co-cultured with DCs that had been pulsed with TLs with or without pp65. PBMCs from sera-negative donors were used to control for CD8 T cell activation independent of pp65. Soluble IFNγ in the tissue culture supernatant was quantified as a measure of CD8 T cell activation. There was a background of 50-200 pg/ml of IFNγ detected in the supernatant when TLs were pulsed in the absence of pp65, possibly due to activation of T cells or natural killer (NK) cells irrespective of pp65 (FIG. 8B). There was no significant difference in elaborated IFNγ between the non-pulsed and lysate-pulsed PBMCs from sera-positive donors, ruling out reactivity to CMV antigens in the lysate, demonstrating negligible expression of CMV antigens in TLs (Cobbs C S, Harkins L, Samanta M, et al. Human cytomegalovirus infection and expression in human malignant glioma. Cancer Res 2002; 62: 3347-50). As expected, PBMCs from sera-positive donors primed with pp65 alone (no TLs) elaborated IFNγ at levels 2-4 fold above background, whereas sera-negative donor PBMCs did not respond to pp65. Thus, sera-positive donor PBMCs displayed a phenotype consistent with immunological memory to CMV, allowing the inventors to measure how TLs could change the response to a defined CD8 T cell epitope.

PBMCs primed with pp65 mixed with 5% $O_2$ TLs elaborated twice the amount of IFNγ compared to pp65 alone. In marked contrast, 20% $O_2$ TLs significantly suppressed pp65-dependent IFNγ secretion (FIG. 8B). In order to confirm that pp65-specifc CD8 T cells were the main source of IFNγ, flow cytometry was conducted to assess IFNγ expression specifically in $CD8^+pp65$-pentamer$^+$ cells (FIG. 8C). Consistent with measured soluble IFNγ, $CD8^+pp65$-pentamer$^+$ cells primed by 5% $O_2$ TLs plus pp65 produced more IFNγ on a per-cell basis relative to all other groups. Taken together, these data demonstrate that 5% $O_2$ TLs have intrinsic adjuvant activity, independent of the amount of TAA expressed. It is noteworthy that these findings paralleled what the inventors recently reported using more precise mouse immunology reagents and established glioma cell lines; namely that 5% $O_2$ TLs increased the presentation of exogenous ovalbumin on MHC I and enhanced antigen-specific CD8 T cell activation, whereas 20% $O_2$ TLs were suppressive to CD8 T cell priming and alternatively promoted antibody responses (Olin M R, Andersen B M, Zellmer D M, et al. Superior efficacy of tumor cell vaccines grown in physiologic oxygen. Clin Cancer Res; 16: 4800-8).

In summary, the present data demonstrate that tissue culture oxygen functions as a master "immunologic switch" by simultaneously regulating the expression of TAA and factors that modulate DC-mediated priming of CD8 T cells. By selecting for expression of TAA that are more abundant on the tumor in situ, the inventors show that oxygen can be exploited to prime CD8 T cells with greater specificity to targets abundant in the tumor in situ. A separate and equally important finding is that tumor cells grown in physiologic oxygen are inherently more immunogenic to CD8 T cells through a mechanism that is independent of co-stimulation but involves enhancement of CD8 T cell priming A third consideration is that growing primary glioma cells in 1-7% $O_2$ increased cancer stem cell markers in several previous studies (Platet N, Liu S Y, Atifi M E, et al Influence of oxygen tension on CD133 phenotype in human glioma cell cultures. Cancer Lett 2007; 258: 286-90; McCord A M, Jamal M, Shankavaram U T, Lang F F, Camphausen K, Tofilon P J. Physiologic oxygen concentration enhances the stem-like properties of CD133+ human glioblastoma cells in vitro. Mol Cancer Res 2009; 7: 489-97; Li Z, Bao S, Wu Q, et al. Hypoxia-inducible factors regulate tumorigenic capacity of glioma stem cells. Cancer Cell 2009; 15: 501-13), showing that the T cells primed are better suited to eradicate cancer stem cells in situ. Vaccines made by expansion of primary tumor cells in physiologic oxygen serve as a powerful system to induce clinically useful anti-tumor immune responses.

EXAMPLE 3

GBM6-AD cells can be grown to generate apoptotic bodies to pulse onto autologous dendritic cells to make a vaccine.

Production of Dendritic Cells.

Peripheral blood mononuclear cells (MNCs) are collected with an FDA-licensed apheresis instrument using established, standard collection procedures. Sterile technique is followed to prevent contamination of the collection. The cells are seeded in a tissue culture flask or cell factory at a viable seeding density of 1.0E+05-1.5E_05 and incubated at 37° C., 5% $CO_2$, On day +3, 20% total volume of culture medium supplements with IL-4 and GM-CSF (1,000 IU/mL) is added to the cells. On day +6 the cells are matured by adding GM-CSF (1,000 IU/mL), ILlbeta (25 ng/mL) TNF-alpha (50 ng/mL), IFN-alpha (10,000 IU/mL), IFN-gamma ((1,000 IU/mL), and Poly-IC (20 μg/mL) and incubating (37° C., 5% $CO_2$) until day +8. A brain tumor apoptotic body (1 apoptotic cell per iDC) is added on day 6 as well. Mature, pulsed alpha-type 1 polarized DCs are harvested from culture using TrypLE Select on day +8 and cryopreserved in Plasmlyte-A, 5% human serum albumin (HSA), and DMSO (10% final concentration).

Brain Tumor Stem Cell Processing.

A single cell line derived from an adult patient with glioblastoma multiforme was tested prior to acceptance into the MCT facility. Testing included mycoplasma (PTC) and sterility; results were satisfactory. Cells were then expanded in serum-free neural stem cell medium (DMEM/F12, B-27 Supplement, N-2 Supplement) with EGF (20 ng/mL final concentration) and bFGF (2 ng/mL final concentration) at 37° C., 5% CO2, and 5% $O_2$. The culture was split as cells formed spheres at approximately 3-5 days using TrypLE Select and mechanical dissociation. Cells were re-suspended in serum-free neural stem cell medium with EGF (20 ng/mL final concentration)/bFGF (2 ng/mL final concentration) and continued through culture until a sufficient amount of cells were expanded for the MCB. The cells were then washed in DPBS and cryopreserved in cryopreservation medium (Plasmlyte-A, 5% human serum albumin (HSA), and DMSO (10% final concentration)).

Samples of the MCB are expanded in a manner consistent with the MCB to establish a working cell mass which is frozen using a controlled-rate freezer. A portion of the mass is then be thawed and subjected to nebulization, and the resultant bulk whole cell lysate is irradiated (200 Gy) and adjusted to approximately 2 mg/mL. It is then be aseptically transferred into vials at approximately 1.2 mg in 600 μL. The vials containing lysate are frozen using a controlled-rate freezer and then stored at ≤−150° C. until distribution for administration.

EXAMPLE 4

Treatment Plan.

Vaccine preparation takes approximately 4 weeks from the time of leukapheresis.

Leukapheresis—Autologous Dendritic Cell Source.

Autologous DCs are obtained from peripheral blood mononuclear cells (PBMCs) from each patient by leukapheresis. The collection is performed using standard collections techniques. PBMCs are collected using a Fenwal CS-3000® Plus blood cell separator (#4R4538) with granulocyte separation chamber and small volume collection chamber (SVCC) (Fenwal Division, Baxter Healthcare, Deerfield, Ill.).

PBMCs are transported immediately to the University of Minnesota Molecular and Cellular Therapy (MCT) Facility for processing. In patients where the vaccine supply is depleted before planned treatment end is reached, a 2nd leukapheresis may be done to obtain cells for additional vaccine production. The need for and timing of this collection is determined on an individual patient basis.

Vaccine Preparation.

The autologous PBMCs will be processed as summarized in FIG. 9. A brain tumor stem cell line derived from a glioblastoma multiforme is maintained at the Molecular and Cellular Therapeutics (MCT) Facility and processed as a source of allogeneic tumor antigen. DC cultures containing $10^7$ to $10^8$ cells are exposed to tumor lysate from $4 \times 10^6$ BTSCs. Pulsed DCs are frozen in individual aliquots until use.

Dendritic Cell-Brain Tumor Stem Cell Vaccination/Imiquimod.

Vaccination is administered on an outpatient basis every 2 weeks during the first 8 weeks then every 4 weeks for 10 additional vaccinations Imiquimod is applied topically at the site just prior to vaccination and again 24 hours later. Patients are observed for 30 minutes after vaccination for immediate adverse events, either systemic or local at the injection sites.

Imiquimod Application.

Imiquimod is marketed as 5% Aldara cream in 250 mg packets, providing a total dose of 12.5 mg per packet and sufficient to cover 20 square centimeters. The contents of ½ of a packet is applied as a thin film to cover approximately 10 square centimeters of skin in the area of the planned vaccination. The Imiquimod is rubbed in well. The leftover Imiquimod is disposed of with a new packet used for each application.

Imiquimod is reapplied in an identical manner at the vaccination site 24 hours (+/−2 hours) later.

Vaccine Administration Plan.

The vaccine is administered at the assigned dose via intradermal injections in 0.5 ml PBS in the shoulders near the back of the neck to facilitate trafficking of the DCs to the cervical lymph nodes. Vaccination is delayed by 1 week if on the day of the planned vaccination the patient has a fever of >101° F. (38.3° C.) or is receiving steroids. A delay of greater than 1 week will result in the patient being discontinued from further vaccinations. Patients are observed for 30 minutes after each injection for immediate adverse events, either systemic or local at the injection site. Patients are followed-up at 48 hours (+/−4 hours) after each vaccine for adverse events.

FIG. 10 is an MRI scan showing tumor regression following vaccination with autologous dendritic cells pulsed with irradiated GBM6-AD apoptotic bodies. This demonstrates therapeutic proof of concept in a human subject, which is novel for an allogeneic glioma cell.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-tumor composition comprising an adherent glioblastoma GBM6-AD stem cell, wherein the adherent glioblastoma GBM6-AD stem cell is ATCC® Patent Deposit Designation PTA-11498.

2. The anti-tumor composition of claim 1, wherein the GBM6-AD cells are lysed or irradiated.

3. The anti-tumor composition of claim 1, further comprising a physiologically-acceptable, non-toxic vehicle.

4. The anti-tumor composition of claim 1, further comprising an adjuvant.

5. The anti-tumor composition of claim 4, wherein the adjuvant is a CpG ODN, Poly ICLC, Annexin A2, a TLR ligand, Imiquimod, or a non-TLR ligand that stimulates an immune response.

6. The anti-tumor composition of claim 5, wherein the adjuvant is a TLR ligand, and the TLR Ligand is a TLR7, TLR8 or TLR7/8 ligand.

7. The anti-tumor composition of claim 1, wherein the cell or cell lysate is conjugated to a carrier.

8. The anti-tumor composition of claim 7, wherein the carrier is a dendritic cell or a macrophage.

9. The anti-tumor composition of claim 1, wherein the composition is contained in a non-cell carrier.

10. The anti-tumor composition of claim 1, wherein the composition is contained in a liposome.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgtactcgg ctccctgttg                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
attcacgcgg ctgtaccaca                                                 20
```

```
<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccccggcgg caatagca                                                    18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcggcgccgg ggagatacat                                                  20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggtagagga gctggcaagg cgac                                             24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttttcagtag cccgcagccg                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctggccttcc aggatatcgg                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgcacagtgc atacggggct                                                  20
```

```
<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgataagca caacatttgg ctct                                                 24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgatggtctt ccatgtttca ctacc                                                25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgcagcttc gaagcctcac aa                                                   22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggcagcag tcagtgggca gt                                                   22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcggagtca acggatttgg t                                                    21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggatttcca ttgatgacaa gct                                                  23

<210> SEQ ID NO 15
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Leu Val Pro Met Val Ala Thr Val
1               5
```